(12) United States Patent
Zadno-Azizi et al.

(10) Patent No.: US 6,327,772 B1
(45) Date of Patent: Dec. 11, 2001

(54) METHOD FOR FABRICATING A PLANAR EVERSIBLE LATTICE WHICH FORMS A STENT WHEN EVERTED

(75) Inventors: Gholam-Reza Zadno-Azizi, Newark; Kirsten F. Luehrs, Menlo Park; Darin C. Gittings, Sunnyvale; Roman Turovskiy, San Francisco; Brian J. Cox, Cupertino; Brian Shiu, Palo Alto; Michael B. Hayes, Pinole; Craig J. Coombs, Palo Alto, all of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/290,562

(22) Filed: Apr. 13, 1999

Related U.S. Application Data

(60) Division of application No. 08/791,921, filed on Jan. 31, 1997, now Pat. No. 5,907,893, which is a continuation-in-part of application No. 08/593,515, filed on Jan. 30, 1996, now abandoned.

(51) Int. Cl.[7] .................................................. B23P 13/04
(52) U.S. Cl. .............................. 29/557; 29/6.1; 623/1.15
(58) Field of Search .......................... 29/6.1, 6.2, 412, 29/418, 557; 623/1.15, 1.16, 1.18, 12, 900, 901; 606/194; 72/379.2

(56) References Cited

U.S. PATENT DOCUMENTS

| | | |
|---|---|---|
| 2,836,181 | 5/1958 | Tapp . |
| 3,178,732 | 4/1965 | Stibitz . |
| 3,497,928 | 3/1970 | Coen . |
| 3,589,356 | 6/1971 | Silverman . |
| 3,991,767 | 11/1976 | Miller, Jr. et al. . |
| 4,347,722 | 9/1982 | Ulam . |
| 4,441,215 | 4/1984 | Kaster . |
| 4,455,557 | 6/1984 | Thomas . |
| 4,470,415 | 9/1984 | Wozniak . |
| 4,655,771 | 4/1987 | Wallsten . |
| 4,728,328 | 3/1988 | Hughes et al. . |
| 4,822,361 | 4/1989 | Okita et al. . |
| 4,834,755 | 5/1989 | Silvestrini et al. . |
| 4,871,358 | 10/1989 | Gold . |

(List continued on next page.)

FOREIGN PATENT DOCUMENTS

| | | |
|---|---|---|
| 0 518 839 A2 | 12/1992 | (EP) . |
| 0 533 511 A1 | 3/1993 | (EP) . |
| 0 682 922 A1 | 4/1994 | (EP) . |
| 0 689 806 | 5/1995 | (EP) . |
| 2714816 | 1/1994 | (FR) . |
| WO 88/00813 | 2/1988 | (WO) . |
| WO 91/12779 | 9/1991 | (WO) . |
| WO 92/11824 | 7/1992 | (WO) . |
| WO 94/06372 | 9/1993 | (WO) . |
| WO 94/25099 | 11/1994 | (WO) . |
| WO 96/25124 | 8/1996 | (WO) . |

*Primary Examiner*—David P. Bryant
(74) *Attorney, Agent, or Firm*—Sterne, Kessler, Goldstein & Fox P.L.L.C.

(57) ABSTRACT

Methods and articles for fabricating expansive stents having generally cylindrical configurations with a pattern therein include interconnecting portions from a generally planar sheet of material with a central portion. A pattern is formed in the sheet of material around said central portion corresponding to said pattern having interconnecting portions. The pattern has a generally circular outer margin. The pattern is separated from the sheet of material and causes relative movement between the central portion of the pattern and the outer circular margin in a direction perpendicular to the plane of the central portion. The pattern is transformed from one sheet form into one in cylindrical form to provide an expansible stent having a generally cylindrical configuration.

20 Claims, 19 Drawing Sheets

U.S. PATENT DOCUMENTS

| | | |
|---|---|---|
| 4,879,084 | 11/1989 | Parnigoni . |
| 4,907,336 | 3/1990 | Gianturco . |
| 4,921,484 | 5/1990 | Hillstead . |
| 4,954,126 | 9/1990 | Wallsten . |
| 4,976,725 | 12/1990 | Chin et al. . |
| 4,994,066 | 2/1991 | Voss . |
| 5,019,090 | 5/1991 | Pinchuk . |
| 5,037,427 | 8/1991 | Harada et al. . |
| 5,045,070 | 9/1991 | Grodecki et al. . |
| 5,061,275 | 10/1991 | Wallsten et al. . |
| 5,064,435 | 11/1991 | Porter . |
| 5,073,694 | 12/1991 | Tessier et al. . |
| 5,104,399 | 4/1992 | Lazarus . |
| 5,127,919 | 7/1992 | Ibrahim et al. . |
| 5,171,305 | 12/1992 | Shickling et al. . |
| 5,234,457 | 8/1993 | Anderson . |
| 5,344,426 | 9/1994 | Lau et al. . |
| 5,421,955 | 6/1995 | Lau et al. . |
| 5,443,499 | 8/1995 | Schmitt et al. . |
| 5,476,508 | 12/1995 | Amstrup . |
| 5,522,881 | 6/1996 | Lentz . |
| 5,540,713 | 7/1996 | Schnepp-Pesch et al. . |
| 5,591,197 | 1/1997 | Orth et al. . |
| 5,609,627 | 3/1997 | Goicoechea et al. . |
| 5,707,388 | 1/1998 | Lauterjung . |
| 5,709,713 | 1/1998 | Evans et al. . |
| 5,735,892 | 4/1998 | Myers et al. . |
| 5,741,327 | 4/1998 | Frantzen et al. . |
| 5,746,765 | 5/1998 | Kleshinski et al. . |
| 5,755,772 | 5/1998 | Evans et al. . |
| 5,755,781 | 5/1998 | Jayaraman . |
| 5,758,562 | 6/1998 | Thompson . |
| 5,776,161 | 7/1998 | Globerman . |
| 5,836,964 | 11/1998 | Richter et al. . |
| 5,919,225 | 7/1999 | Lau et al. . |

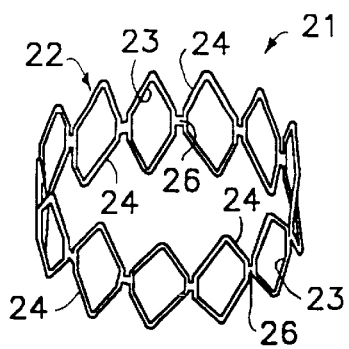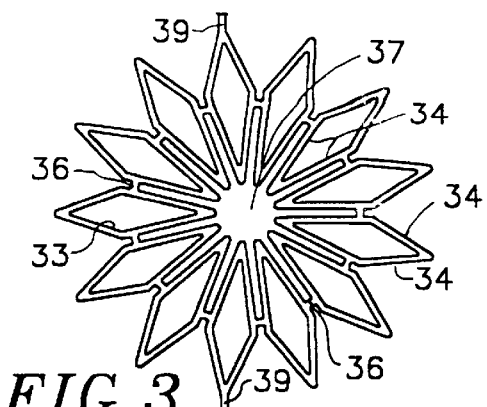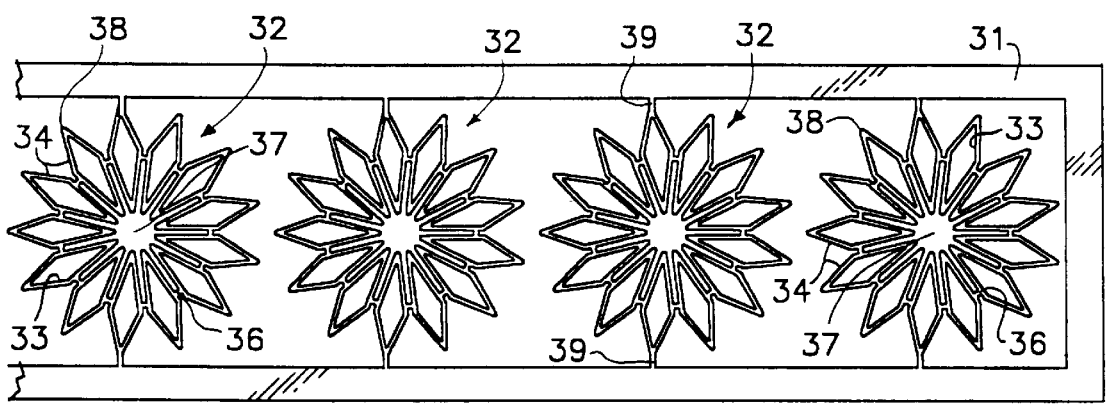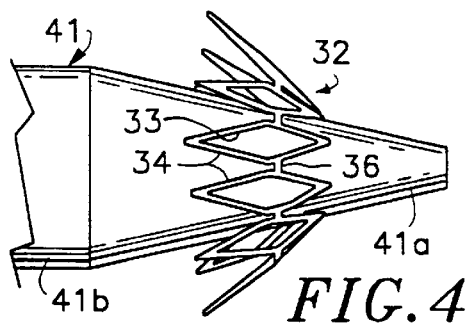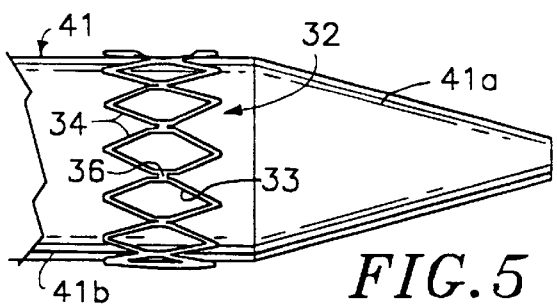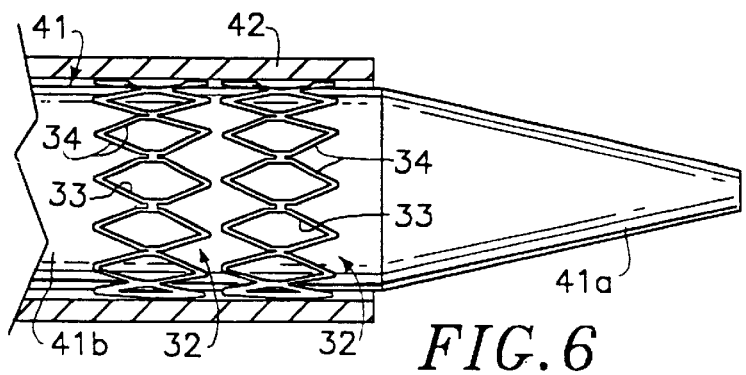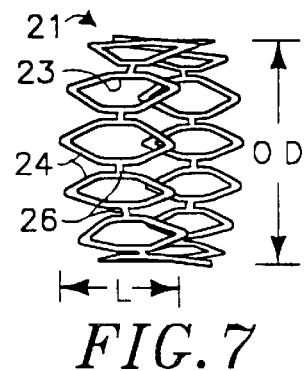

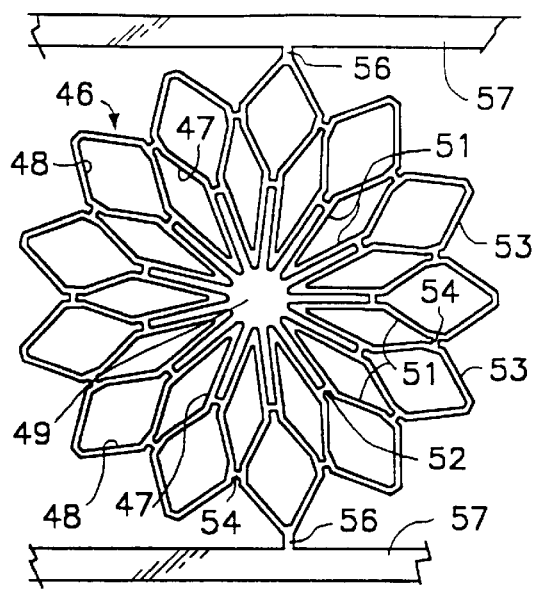
*FIG.8*
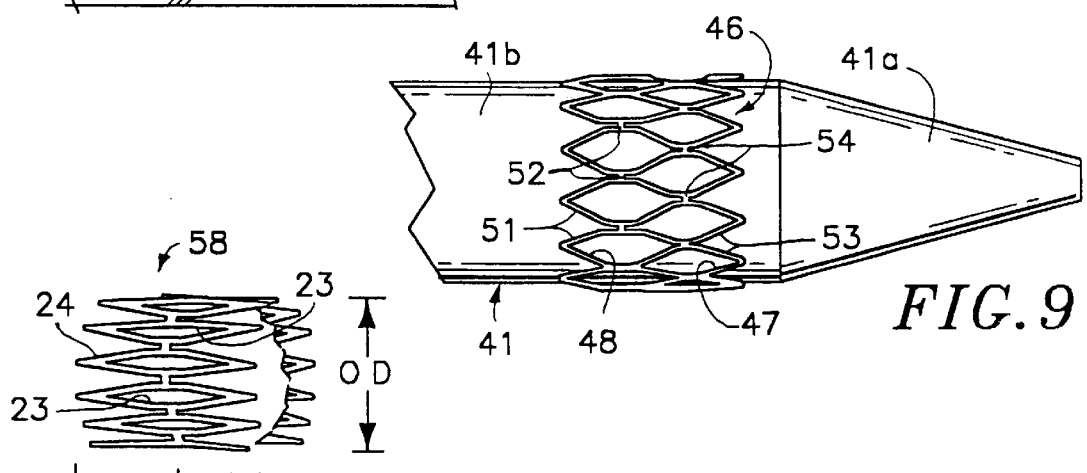
*FIG.9*
*FIG.10*
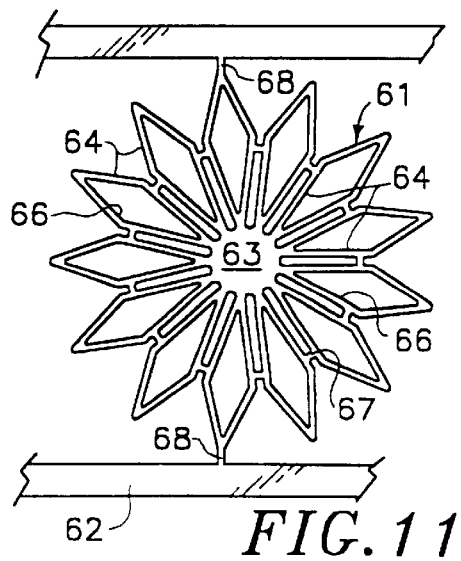
*FIG.11*
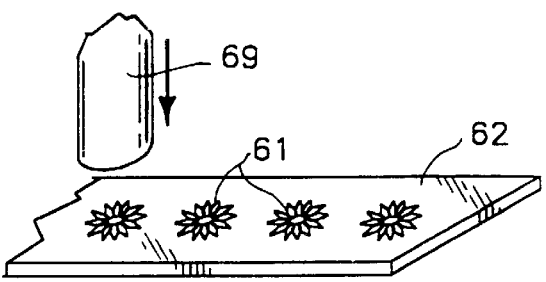
*FIG.12*
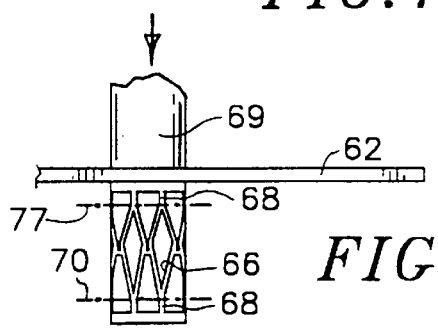
*FIG.13*

METHOD FOR FABRICATING A PLANAR EVERSIBLE LATTICE WHICH FORMS A STENT WHEN EVERTED

CROSS-REFERENCE TO RELATED APPLICATION

The present application is a divional of U.S. application Ser. No. 08/791,921, filed Jan. 31, 1997, now U.S. Pat. No. 5,907,893, which is a continuation-in-part of Ser. No. 08/593,515, filed on Jan. 30, 1996, now abandoned. The full disclosure of these applications are incorporated herein by reference.

BACKGROUND OF THE INVENTION

1. Field of the Invention

The present invention relates generally to stents and other prostheses intended for implantation in blood vessels and other body lumens. In particular, the present invention relates to methods and articles for the fabrication of such stents.

The use of stents and other luminal prostheses is often indicated when there is desire to maintain patency of a body lumen. Stents have commonly been used in blood vessels, the ureter, and the biliary duct, for the treatment of conditions which can result in luminal obstruction. Of particular interest to the present invention, vascular stents have demonstrated significant success in inhibiting restenosis following angioplasty and other primary interventional treatments in the vasculature. Lined stents, often referred to as vascular stent grafts or prostheses, hold great promise for the reinforcement of blood vessels for the treatment of aneurysms and lining of blood vessels for the treatment of occlusive disease among other conditions. In the case of aneurysms, the stent acts as a scaffold or framework for supporting the liner within the blood vessel to define an artificial lumen therethrough. In the case of occlusive disease, the stent maintains lumenal patency while the liner inhibits cellular intrusion into the lumen.

Vascular stents are typically delivered in a radially reduced or constrained configuration and expanded in situ at the target site. The stents may be deformable and balloon-expanded at the target site. Alternatively, the stents may be formed from a resilient material and released from constraint to self-expand at the target site. In a third general approach, the stents are formed from a shape-memory alloy and induced to expand at the target site by exposure to a temperature change. In all such cases, the stent will usually comprise a network or lattice of structural elements which permits configuration in both the radially-reduced and the radially-expanded geometries. One common geometry comprises a plurality of lozenge-shaped or diamond-shaped elements which are joined in a ring and may be expanded from a small diameter configuration to a large diameter configuration. Other common geometries include helically wound wires and filaments, zig-zag rings, serpentine rings, and numerous combinations and derivations of these geometries.

Regardless of the particular stent geometry chosen, manufacture of the stent presents a number of technical challenges. The stents have very small dimensions, often with diameters of 1 mm and below, and may be formed from metals and alloys that are difficult to fabricate, such as shape memory alloys and stainless steel alloys having specific properties. It will be appreciated that the stents which are produced must have highly uniform expansion characteristics, and thus the fabrications methods should result in stents having highly uniform mechanical properties. Moreover, the dimensions must meet very close tolerances and the surface finishes of the stents must be non-injurious and non-thrombogenic.

The most common methods for producing vascular and other stents start with a tube which is then cut or otherwise patterned to have the desired geometry. In many cases, particularly with shape memory alloys, it will be further necessary to heat-treat the resulting stent in order to gain desired expansion properties. Cutting of the tube stock starting material can be effected in a variety of ways. Most commonly, laser cutting is employed. Laser cutting, however, results in significant thermal stresses on the material which can be particularly troublesome when producing shape memory alloy stents. Chemical etching of the tube starting materials have also been proposed. Patterning and etching of tubes, however, is very difficult and expensive to perform.

For these reasons, it would be desirable to provide improved methods and articles for manufacturing cylindrical stents. Such improved methods should preferably be compatible with a wide variety of starting materials, including shape memory alloys, stainless steel alloys, and other materials from which stents are commonly performed. Such methods and articles, moreover, should preferably expose the materials to minimum thermal and other stresses, thus enhancing the dimensional and physical stability of the resulting stents. The present invention will address at least some of these objectives.

2. Description of the Background Art

Methods for laser cutting tube stock are described in U.S. Pat. No. 5,073,694. Methods for etching tube stock to produce vascular stents are described in U.S. Pat. No. 5,421,955. Methods for fabricating stents by winding a serpentine element over a cylindrical mandrel are described in U.S. Pat. No. 5,019,090.

SUMMARY OF THE INVENTION

The present invention provides improved methods for fabricating cylindrical stents from planar articles. The planar articles comprise networks of interconnected elements, and the methods comprise the reforming the planar networks into a cylindrical wall which may form all or part of a stent or other luminal prosthesis. Usually, the planar networks will comprise an annular lattice of element(s), where the lattice may be formed as a continuous path or as a discontinuous path. Usually, the lattice will be continuous and will comprise interconnected elements joined in a complete annular ring. Exemplary geometries include serpentine rings, a plurality of closed peripheral structures, such as interconnected lozenge (diamond)-shaped structures, and the like. Exemplary discontinuous lattices include spirals having a radially inward end and radially outward end. Such spirals may have secondary geometries, such as a superimposed serpentine pattern, and in some cases may be arranged in a rectilinear pattern (in addition to curved spiral patterns).

In the case of annular lattices, the reforming step will comprise everting the annular lattice to the desired cylindrical configuration. By "everting" it is meant that the inner peripheral edge of the annular structure is expanded radially outward relative to the outer peripheral edge of the structure. It will be appreciated that such eversion may be effected either by expanding the inner peripheral edge, contracting the outer peripheral edge, or a combination of both such steps. Often, the everting step will be performed over the exterior surface of a cylindrical mandrel. Alternatively, the everting step could be performed by introducing the annular lattice into a cylindrical tube or lumen, or by other equivalent techniques.

The reformed annular lattices will assume a radially expansible, typically cylindrical, configuration. By "radially expansible," it is meant that width (diameter in the case of cylindrical structures) can be expanded and/or contracted after reforming. Usually, the structures will be either malleable, in which case they are expanded by application of a radially outward force in their lumens, or self-expanding in which case the initial geometry will be "expanded" and will be radially constrained prior to use. The latter type of stents are usually formed from shape memory alloys or resilient stainless steel and referred to as "self-expanding stents."

The planar articles of the present invention may be formed in a variety of ways. Usually, they will be formed by patterning a planar sheet of material. Exemplary patterning steps include photochemical etching (usually performed as part of a photolithography process), cutting, stamping, and the like. In an exemplary technique, a plurality of sheets of material may be stacked and simultaneously cut in order to form a plurality of eversible structures in a single fabrication process. Often, at least five sheets of material will be simultaneously cut, preferably at least ten sheets of material, more preferably at least twenty sheets of material, and frequently twenty-five or more sheets of material. The cutting may be performed by conventional techniques, such as electrical discharge machining (wire or plunge EDM), laser cutting, water or abrasive jet cutting, and the like. Preferred is the use of EDM since cutting is very precise and achieved at lower temperatures, leaving fewer thermal artifacts in the resulting articles.

In a specific example, the planar articles may be fabricated from rods of material, usually cylindrical rods. The rods will be sliced in a direction transverse to the axis of the rod in order to form sheets and articles having a desired thickness. The planar geometries of the articles may be formed either before, after slicing, or as a combination of steps performed before and after slicing. It has been found that articles formed by slicing rod stock often have improved uniformity in their grain structure. Moreover, it has been found that dimensional stability is improved in planar articles which are formed from sliced rod stock, particularly after complex patterning.

As an alternative to patterning a flat sheet of material, the planar network of interconnected elements can be formed from one or more discrete elements by arranging the elements(s) into the desired geometry. For example, the planar network can be formed from a single filament of material by folding, curving, or otherwise shaping the material into the desired pattern. In some cases, the single filament can be formed into a continuous path by securing the ends thereof together, e.g. by welding. As a still further alternative, the planar network can be formed by joining a plurality of discrete elements into the planar network, e.g. by welding the elements together. The discrete elements can be linear elements, e.g. beams or struts; curved elements; closed peripheral structures; or the like. While forming the planar network from discrete elements which are welded or otherwise joined together is generally less preferable, it may find specific uses within the scope of the present invention.

The articles may be composed of any material suitable for forming vascular and other luminal stents. Most commonly, the articles will be formed from metals or plastics, most commonly being formed from metals. Exemplary metals include shape memory alloys, such as nickel-titanium alloys, stainless steel alloys, platinum, tantalum, titanium, elgiloy, and the like. For vascular stents, the thickness of the articles, e.g. the thickness from the sheet of material from which they are formed, will be in the range from 0.1 mm to 1.0 mm, usually from 0.25 mm to 0.5 mm. For annular geometries, the outer periphery of the articles will usually be circular, often having a diameter in the range from 10.0 mm to 100.0 mm, usually from 10.0 mm to 50.0 mm. The article will then be reformed, typically by an everting step as described above, to form a cylindrical wall having prior to expansion a diameter in the range from 0.5 mm to 50.0 mm, often from 1.0 mm to 25.0 mm, typically from 1.0 mm to 15.0 mm. After expansion, the cylindrical wall portion will have a diameter in the range from 1.0 mm to 75.0 mm, often from 2.0 mm to 50.0 mm, typically from 5.0 mm to 20.0 mm.

During or subsequent to the everting step, the article may be treated in order to change certain physical properties. For example, the article may be heat treated in order to reduce stress, change elasticity, change appearance, or the like. In the case of shape memory alloys, it will usually be necessary to heat treat the article in order to provide the desired memorized shape as well as to set the transition temperature. The articles will also be finished as necessary, e.g. deburred, coated with biocompatible materials, and otherwise treated to permit human and animal implantation. Such processing steps may be conventional and do not form part of the present invention.

Articles according to the present invention comprise eversible planar structures. The eversible planar structures can be everted into a cylindrical wall portion of a cylindrical stent, where the structure comprises a planar network of interconnected elements which become radially expansible after eversion. The interconnected elements are usually arranged as an annular lattice and the interconnected elements are usually joined in at least one continuous annular path. For example, the continuous annular path may be an annular serpentine ring, such as a zig-zag ring or a ring comprised of U-shaped segments. Alternatively, the continuous path may comprise a plurality of lozenge-shaped elements, typically having axes which are aligned radially within the annular lattice. Adjacent lozenge-shaped elements are connected to each other, typically by tabs located along a common diametric line within the annular lattice. The eversible structure may comprise two or more successive annular rows of interconnected elements. Alternatively, the eversible structure may comprise one or more elements which are not connected in a continuous path in the annular region. For example, the structure may comprise a spiral which becomes a radially expansible helical coil after eversion. The spiral may further comprise a serpentine structure superimposed over the spiral. Such eversible structures may be composed of any of the materials described above as well as fabricated by any of the methods described above.

BRIEF DESCRIPTION OF THE DRAWINGS

FIG. 1 is a perspective view of a stent manufactured by the method of the present invention.

FIG. 2 is a plan view of a strip of sheet metal having a plurality of planar spaced-apart patterns therein in which each of the patterns is utilized to make a cylindrical stent of the type shown in FIG. 2.

FIG. 3 is an enlarged view of one of the patterns shown in FIG. 2.

FIG. 4 is a side-elevational view showing the way in which a mandrel is used to form the cylindrical stent and showing the stent in an intermediate position as it is being formed from the planar pattern shown in FIG. 2 and into the cylinder as shown in FIG. 1.

FIG. 5 is a view similar to FIG. 4 but showing the stent on the mandrel in its final cylindrical configuration and completely transformed from a planar configuration to a cylindrical configuration.

FIG. 6 is a side-elevational view showing the manner in which a plurality of stents are carried by the mandrel and enclosed within a sleeve during heat treatment of the stents.

FIG. 7 is a perspective view of a stent after it has been completed in accordance with the present invention.

FIG. 8 is a plan view of a double-diamond pattern formed in a sheet to provide a stent in accordance with the present invention.

FIG. 9 is a side-elevational view showing the stent after it has been formed onto a mandrel from the planar pattern shown in FIG. 8 to provide a cylindrical stent having the double-diamond pattern.

FIG. 10 is a side-elevational view showing a stent in which the diamond shaped patterns have been elongated to provide s stent which has a length greater than the outside diameter.

FIG. 11 is a plan view of a planar pattern provided in a sheet of nickel titanium alloy.

FIG. 12 is an isometric view showing a sheet of nickel titanium alloy with a plurality of spaced-apart patterns of the type shown in FIG. 11 incorporated therein and being punched out in a punch press.

FIG. 13 is a side-elevational view showing a deep drawn cap formed from one of the patterns shown in FIG. 12.

DESCRIPTION OF THE SPECIFIC EMBODIMENTS

Figure 3A:
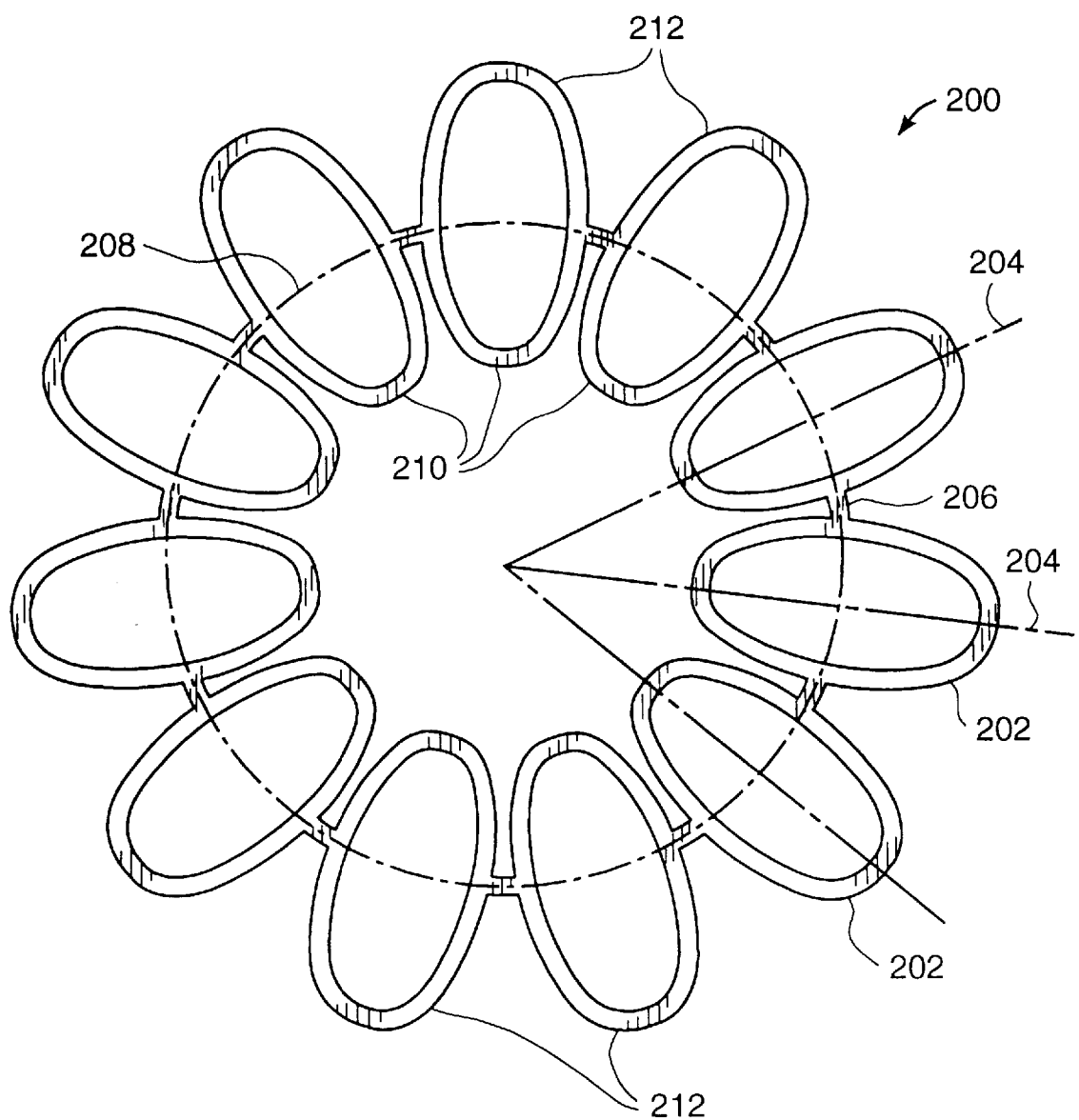
FIG. 3A illustrates a flat stent pattern similar to that shown in FIG. 3, except that oval-shaped elements are provided in place of the diamond-shaped elements of FIG. 3.

A method for making expansible stents having a generally cylindrical configuration with a pattern therein having interconnecting portions in accordance with the present invention from a sheet of material having a central portion comprises forming around said central portion in the sheet of material a pattern having a generally circular outer margin and corresponding to said pattern having interconnecting portions, separating the pattern from the sheet of material and causing relative movement between the central portion of the pattern and the outer margin of the pattern in a direction perpendicular to the plan of the central portion to transform the pattern into a cylinder to provide the expansible stent having the pattern therein. An appropriate heat treatment for the stent may thereafter be provided when desired.

More specifically, an exemplary method of the present invention is for making a stent 21 having a generally cylindrical configuration and having a pattern 22 therein to impart radial flexibility to the stent. In the pattern 22 a single row of lozenge or diamond-shaped openings 23 are provided in which the diamond-shaped openings are defined by elongate elements 24 with four of the same being provided for the four sides of the diamond-shaped opening 23 with the elements 24 abutting end to end and being continuous. The diamond-shaped openings 23 are lozenge-shaped and generally define a plane figure with four sides with two opposite obtuse angles and two opposite acute angles. As shown, two of the legs can have a length which is less than the length of the outer two legs. The elongate elements 24 forming each of the diamonds are connected to immediately adjacent diamonds on opposite sides by interconnecting portions (tabs) 26 formed of the same material as the elongate elements 24. As shown, the interconnecting portions 26 are near the apices of the obtuse angles formed by the elongate elements 24. It should be appreciated that more than four sides can be provided for defining the openings 23 if desired and still encompass the features of the present invention. Because of the diamond-shaped configuration, it can be seen that the cylindrical stent 21 can be compressed radially and at the same time provide outwardly facing radial forces to maintain the patency of the lumen of the vessel of a human body in a manner will known to those skilled in the art.

Although the diamond-shaped elements of FIG. 3 will frequently be preferred, it is possible to substitute a variety of other closed peripheral structures for the diamonds. For example, the closed peripheral structures can be circular, oval, polygonal, irregular, or the like. Indeed,, the only requirement is that the structure be capable of expanding in width to accommodate expansion of the resulting cylindrical stent structure after eversion. For example, an exemplary planar reversible article 200 which can be everted into a cylindrical wall portion may comprise a plurality of oval-shaped elements, as illustrated in FIG. 3A. As with the diamond-shaped elements of FIG. 3, the ovals 202 are arranged so that they have elongate axes 204 aligned radially and are connected by tabs 206 which lie along a common diametric line 208. Such a structure is particularly convenient since the oval elements 202 (or the diamond-shaped elements of FIG. 3) may be everted about the diametric line 208, with the inner peripheral ends 210 moving away from each other in a radially expanding direction and/or the outer peripheral ends 212 moving closer to each other in a radially collapsing pattern. Specific everting techniques are described in more detail below.

Figure 3B:
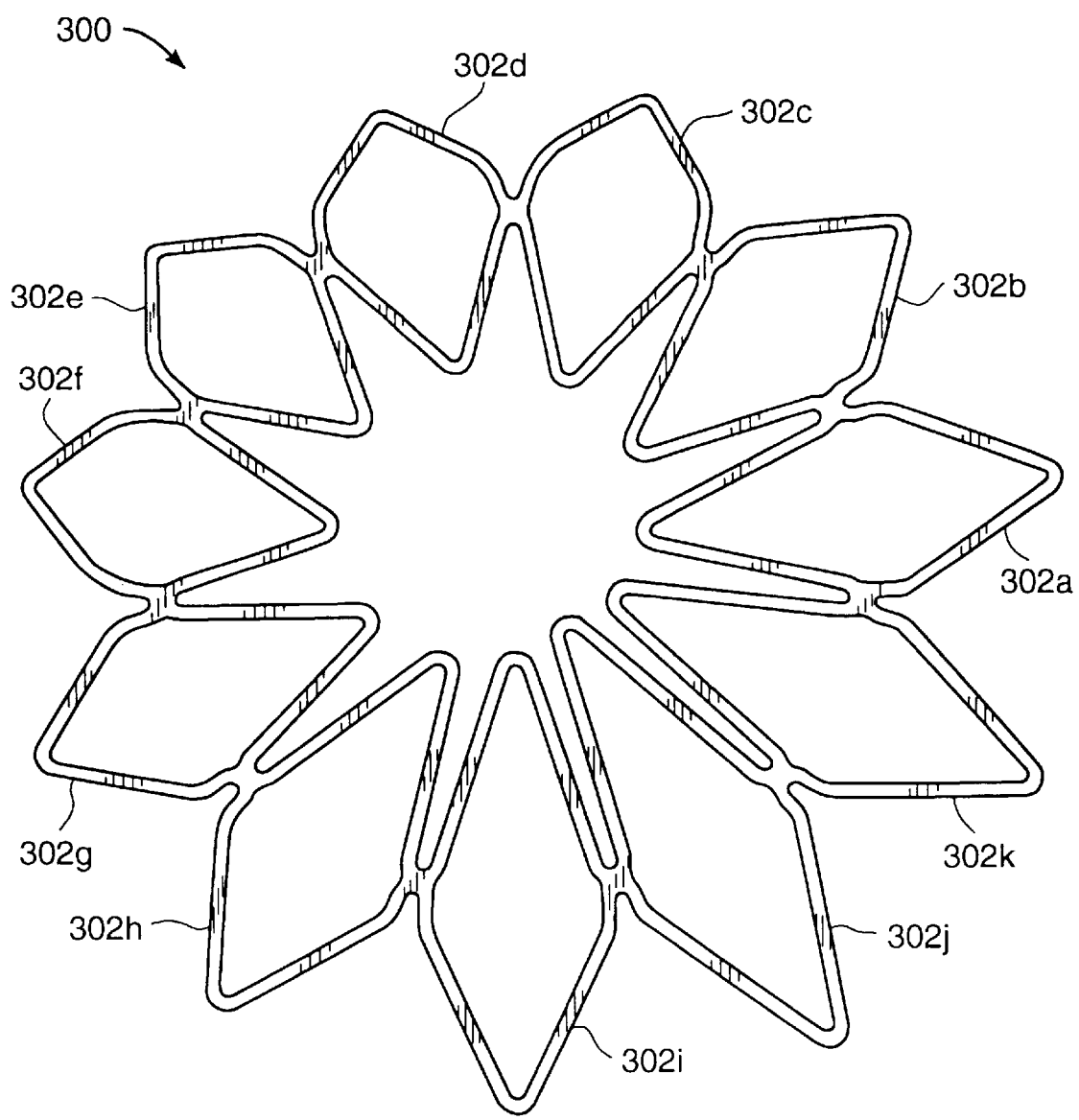
FIG. 3B illustrates still another alternative flat stent pattern similar to that illustrated in FIG. 3, where the interconnected diamond-shaped elements have different lengths in the radial direction.

Another planar eversible article 300 is illustrated in FIG. 3B. The article 300 comprises eleven lozenge (diamond)-shaped elements 302a–302k. The principle distinction of the article 300 is that the various diamond-shaped elements 302a–302k have different radial lengths. The radial length in the planar configuration of FIG. 3B will become the axial length after the article 300 is everted. Thus, the cylindrical stent structure which results from everting planar article 300 will have a shorter length on one side and a longer length on the other side, i.e. the ends will appear angled or chamfered. Such chamfered structures will be useful in treating asymmetric lesions and/or for joining successive stent structures in order to make a curved multi-segmented stent. Optionally, the ends of the cylindrical wall which results from everting structure 300 of FIG. 3B may be joined together, e.g. by tying, welding, or the like.

In accordance with the method of the present invention for manufacturing a plurality of expansible stents of the type shown in FIG. 1, a sheet 31 of a suitable material (as described below) is provided. The sheet 31 can be formed of an elongate strip in which the strip has a width which is slightly greater than the width of the patterns 32 formed therein with the patterns 32 being spaced longitudinally of the strip as shown in FIG. 2. The sheet 31 can have a suitable starting thickness as for example from 0.005" to 0.040" which may thin down during the steps hereinafter described to a final thickness of 0.003" to 0.030". The material utilized for the sheet 31 should be of a material which is useful in stents, as for example it should be of a biocompatible material. Materials such a stainless steel can be utilized as well as various nickel titanium alloys. In many cases, it is desirable to utilize the nickel titanium alloys because they have a much greater elasticity than stainless steel. However, iron-based shape memory alloys can also be utilized. For example, Nitinol alloys have an 8% elasticity versus approximately a half percent elasticity for stainless steel. Additional characteristics of nickel titanium alloys which are useful in the present invention are thereinafter described.

The patterns 32 correspond generally to the pattern 22 shown in FIG. 1. As shown in FIGS. 2 and 3, the patterns 32 are provided with a plurality of diamond-shaped openings 33 which are diamond or lozenge-shaped as hereinbefore described. The openings 33 are defined by elongate elements 34 which are formed from the sheet 31 and therefore have a substantially rectangular cross section with four of the elongate elements 34 forming a diamond-shaped opening 33 with two opposite obtuse angles and two opposite acute angles and with interconnecting portions 36 interconnecting the elongate elements at the portions of the elongate elements 34 forming the obtuse angles. Thus, there is provided a plurality of diamond-shaped openings 33 circumferentially disposed around a central opening 37 and in which the outermost acute angles lie in a circle to provide an outer generally circular margin 38 which is concentric with the central opening 37. Thus, it can be seen that the arrangement of the elongate elements 34 with interconnecting portions 36 form a geometric circular pattern 32 as shown. The individual patterns 32 remain supported within the sheet 31 by support tabs 39 which are formed from the sheet 31 and which are attached to the outer portions of the elongate elements 34 forming the outermost acute angle of the diamond-shaped openings 33.

The patterns 32 can be formed in any suitable convention manner. For example, they can be formed by photochemical etching, laser cutting, stamping or wire EDM. It can be seen that the construction is such that the patterns can be readily stamped out sequentially by running the same through a punch press with the appropriate dies.

After the patterns 32 have been formed in the sheet 31, individual patterns can be removed from the sheet by severing the tabs 39 carrying the same. Each pattern 32 can be loaded onto a tapered mandrel 41 by inserting the tapered portion 41a of the mandrel 41 through the central opening 37 and causing the central opening to be expanded and to cause the pattern 32 to assume a cone shape as shown in FIG. 4. Continued movement of the pattern 32 over the tapered portion 41a onto the cylindrical portion 41b of the mandrel 41 causes it to move from the intermediate cone shape to assume a generally cylindrical shape as shown in FIG. 5. Thus, it can be seen that relative movement is caused between the central portion of the pattern and the outer circular margin in a direction perpendicular to the plane of the central portion. The cylindrical portion 41b is sized to be of the diameter desired for the stent to be formed from the pattern. It should be appreciated that if desired the transition in the pattern can be accomplished without the use of a mandrel.

Thereafter, additional patterns 32 can be loaded onto the same mandrel and to retain them in a desired maximum diameter to be incorporated therein during the heat treatment. After the desired number of patterns 32 have been loaded onto the mandrel 41, a sleeve 42 of a suitable material such as stainless can be placed over the mandrels and over the patterns 32 to hold the spaced-apart patterns in place on the mandrel. The assembly can then be placed in an oven for heat treatment of the patterns 32 to provide stents having the desired characteristics as well as a memory of the maximum diameter. Typically, nickel titanium alloys can be heat treated or annealed at a temperature ranging from 300° C. to 800° C. with the time of heat treatment ranging from a few seconds to an hour or more. After the patterns have been heat treated as hereinbefore described, the mandrel with the heat treated patterns thereon can be permitted to cool to room temperature after which the sleeve 42 can be removed. The patterns 32 can then be removed from the mandrel to provide the stents 21 of the type shown in FIG. 1.

In addition to passage over the exterior surface of a mandrel, as just described, the planar articles of the present invention can be everted in a number of other ways. For example, they can be fed into the inner lumen of a tubular mandrel, with the radially outward periphery of the article being collapsed to fit into the lumen. Alternatively, they can be everted between coaxial, sliding tubes and/or axially sliding pins which engage radially inward and radially outward points on the articles to effect the eversion.

It should be appreciated that if the patterns are delivered at a high temperature, the patterns can be formed from the planar shape into the cylindrical shape in a single step without the necessity of heat treating them.

If it is desired that the stent be superelastic at room temperature or at body temperature, it is heat treated so that if deformed the stent will have a desire to come back to the shape it was in at the time it was heat treated. Thus, it will have a memory of this shape and size and if compressed from that size and shape, it will self expand to the heat treated shape after it has been released. The nickel titanium superelastic material typically is a binary material such at NI (50.8 WT %) and TI or a ternary alloy such as NiTi—V. For nickel titanium alloys, a binary alloy such as a nickel titanium alloy and a ternary alloy nickel titanium and copper can be utilized. Iron-based shape memory alloys are also good candidates for this application. The stainless steel can be of a suitable material such as 304V. In case of alloys such as stainless steel or titanium alloys, it is possible to obtain the stent 22 without a need to heat treat the pattern 32. The procedure would then be overcoming the elasticity of the material by over-deforming. Also usable are other titanium alloys known to those skilled in the art or composites of the aforementioned alloys. Superelasticity typically can be introduced into a cold-working nickel titanium alloy used for the stent at 350° C. to 500° C. for a period of a few seconds to an hour or more. If a heat treating operation conducted at a high temperature or another thermomechanical process has resulted in a material that has less than the necessary 20–40% cold work, a solution treatment of 700° C. to 800° C. for a period of 10 to 40 minutes followed by rapid quenching in a cold fluid such as water and aging at 300° C. to 500° C. for 5 to 60 minutes can be utilized.

If actuator-type Nitinol material is utilized, two stent forms can be provided with the nickel titanium alloy in its martensitic state at room temperature. In one stent form, the stent is deformed into a small shape and then delivered to the desired location after which the stent can be heated to cause it to expand to its memorized or final state. In the other stent form, the stent is placed in a desired location with mechanical means such as a balloon in a manner well known to those skilled in the art to cause it to expand and to leave the stent in place in its martensitic state. The advantage of such a stent is that in the event it is desired to remove the stent, this can readily be accomplished merely by heating the stent above body temperature to reduce its diameter and to permit its easy removal.

A side-elevational view of the stent 21 is shown in FIG. 7 in which the outside diameter and the length of the stent is given. With the patterns hereinbefore described, typically the length L of the stent is less than the outside diameter OD of the stent.

In FIGS. 8 and 9, there is shown another method for making a stent 46 having a double-diamond pattern, rather than a single diamond pattern. This double-diamond pattern makes it possible to optimize the stiffness of the stent while at the same time providing a stent of greater length without having longer diamond-shaped openings. Thus, there is provided a first circular row of diamond-shaped openings 47 and a second row of diamond-shaped openings 48 with the two rows of openings 47 and 48 forming concentric circles which are also concentric with a central opening 49. The pattern 46 can be formed in the manner hereinbefore described from sheet material of the type hereinbefore described. The first row of diamond-shaped openings 47 are formed by elongate elements 51 of the sheet material forming spaced-apart oppositely-facing obtuse angles which are circumferentially arranged and opposed oppositely facing acute angles which are radially disposed. Interconnecting portions 52 are provided between the elongate elements 51 at the portions forming the obtuse angles. Similarly, the second or outer row of diamond-shaped openings 48 are formed by elongate elements 53 which are also arranged to form oppositely facing obtuse angles disposed circumferentially and oppositely facing acute angles extending radially. Interconnecting portions 54 located at the positions of the obtuse angles in the outer row serve to is interconnect the elongate elements 53. The pattern 46 is supported by tabs 56 in the sheet 57. The pattern 46 can be formed in the manner hereinbefore described. It can be separated from the sheet 57 by severing the tabs 56. The pattern can then be inserted over the mandrel 41 as shown in FIG. 9 to cause a transformation of the pattern from a planar configuration to the cylindrical configuration shown in FIG. 9. This serves to provide the stent 44 having a greater length and which has a double-diamond configuration to provide an optimized stiffness for the stent. The desired rigidity or stiffness can be obtained by varying the design of the diamond-shaped openings. The wider the diamond-shaped openings, the greater the flexibility and the greater the softness. When the diamonds are narrower or smaller, the stent becomes more rigid and less soft.

Another method is shown in FIG. 10 which is used when it is desired to provide a stent 58 which has a length which is greater than the outside diameter of the stent. To accomplish such a method, a stent 21 of the type shown in FIG. 6 is mechanically compressed as shown in FIG. 10 to decrease its outside diameter, for example by 50 percent. This causes elongation of the diamond-shaped openings 23 and increases the length of the stent as represented by a length L which is greater than the outside diameter OD. Thus, in accordance with the present invention to obtain a stent of greater length, it is necessary to start with a stent made in accordance with the present invention having an outside diameter which is at least as great as the desired length after which the stent after it has been positioned can be compressed down into a smaller diameter until the desired length of stent has been obtained. Such a stent with heat treatment will have a memory causing it to want to return to its original shape and thereby applying the desired yieldable radial forces on the vessel in which the stent is used.

Figure 14:
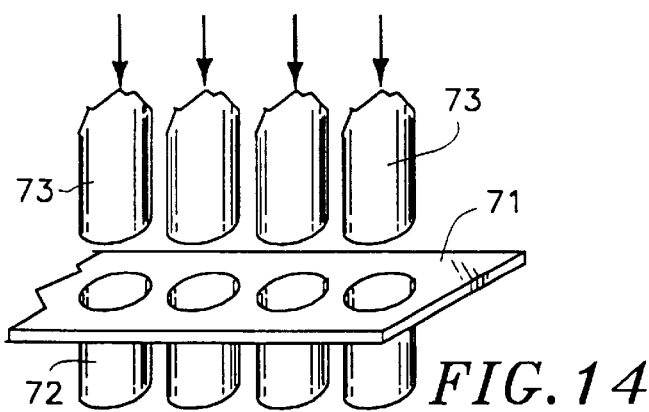
FIG. 14 is an isometric view showing the manner in which a plurality of deep-drawn cups can be formed simultaneously or individually in sequence from a sheet of a nickel titanium alloy.
Figure 15:
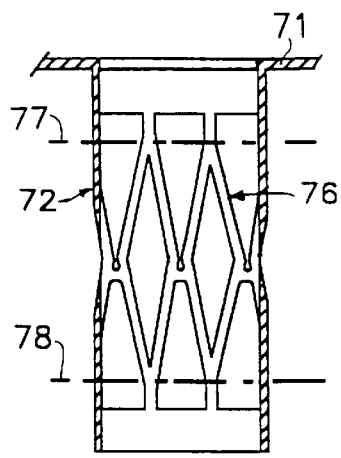
FIG. 15 is an enlarged cross-sectional view showing the manner in which a stent can be made from the deep-drawn cups provided in FIG. 14.

Still another method for making stents in accordance with the present invention is shown in FIGS. 11, 12, and 13. A pattern 61 is provided in a sheet 62. The pattern 61 is very similar to the patterns hereinbefore described with the exception that the central portion 63 is solid rather than being an opening so that the central portion 63 is integral with the elongate elements 64 forming the diamond-shaped openings 66. The elongate elements 64 are provided with interconnecting portions 67. Support tabs 68 are provided to support the elongate elements 64 in the sheet 62. As shown in FIG. 13, a plurality of such patterns 61 can be formed in a sheet 62 in the form of a sheet metal strip in which the patterns are spaced apart longitudinally of the strip. Each of the patterns can then be punched out simultaneously or sequentially by the use of a punch represented schematically at 69 in FIG. 13 to cause deep drawing of the pattern into a die (not shown) to cause the transformation from the planar configuration to a cylindrical configuration in the form of a cup 72 as shown in FIG. 14. After the deep drawing operation has been completed, the punch 69 is removed and the lower portion of the pattern 61 can be removed along the cut line 70. Similarly, the pattern 61 can be removed along the cut line 70. Similarly, the pattern 61 in cylindrical form can be separated from the sheet 62 by severing the same at or adjacent to the plane of the sheet. Thereafter what remains is a stent (not shown) having a cylindrical configuration and having the pattern hereinbefore described therein as in the previous embodiments.

Alternatively if desired, sheet material 71 as shown in FIG. 14 can be utilized and cylindrical cups 72 can be deep drawn from the sheet 71 by punches 73 either simultaneously or sequentially. Thereafter, a diamond-shaped pattern 76 of the type hereinbefore described can be formed into the cylindrical cups 72 by a suitable technique of the type hereinafter described. These patterns can be formed while the cups 72 are attached to the sheet 71, or alternatively the patterns can be formed after the cups 72 have been removed along the cut line 77 and the central portion of the pattern 76 removed along the cut line 78 to provide a cylindrical stent (not shown) of the type hereinbefore described.

The method shown in FIGS. 12, 13, 14, and 15 is particularly desirable for use with sheet material formed of nickel titanium alloys. Typically, nickel titanium alloys have been difficult to form into hypotubes. By punching out individual cups in the form and size of the cylindrical stents desired, it is possible to provide what is, in effect, very short lengths of hypotube which can be converted into stents of the present invention with ease. This eliminates the step of forming nickel titanium alloys into hypotubes which in the past has been quite difficult.

Figure 16:
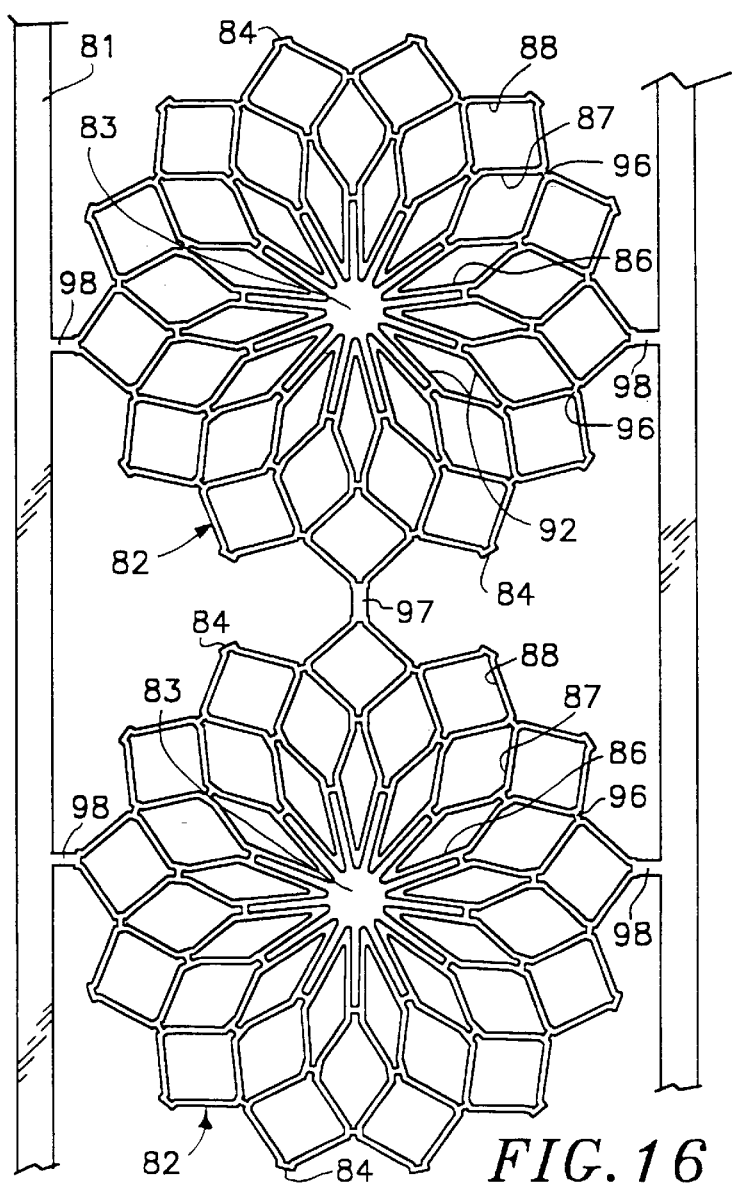
FIG. 16 is a plan view of a pattern formed of a sheet of material which can be utilized for making another stent in tandem in accordance with the method of the present invention.
Figure 17:
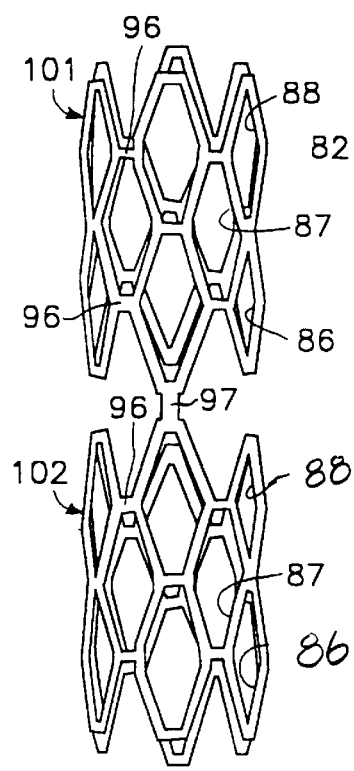
FIG. 17 is a side-elevational view showing tandem stents made from the planar pattern shown in FIG. 16.

Other examples of stents which can be formed with a different type of pattern is shown in FIGS. 16 and 17. The folding operation does not change the thickness. The deep drawing method slightly reduced the thickness depending on the pattern and length. More open structures will reduce less in thickness. In addition, FIGS. 16 and 17 show a method for making a tandem stent in accordance with the present method. There is shown in FIG. 16 a sheet 81 in the form of a strip in which a repetitive pattern 82 is provided. Each of the patterns 82 has a generally circular inner portion 83 and a generally circular outer margin 84. The pattern 82 is formed with three rows 86, 87, and 88 of diamond-shaped openings delineated by elongate elements 92 of the sheet material of the type hereinbefore described. The diamond-shaped openings hereinbefore described have been described as having four sides and the openings 86, 87 and 88 can also be considered to be four-sided diamond-shaped openings. However, as can be seen from FIG. 16, these openings can be considered as having six sides with two additional sides being provided by the truncated distal extremities of the diamond-shaped openings. Interconnecting portions 96 on opposite sides of the pattern 82 support the pattern in the sheet. In addition, there are provided additional interconnecting portions 97 which serve to interconnect two of the patterns 82 into a tandem pattern arrangement. Support tabs 98 support the tandem pattern in the sheet 81.

Figure 16A:
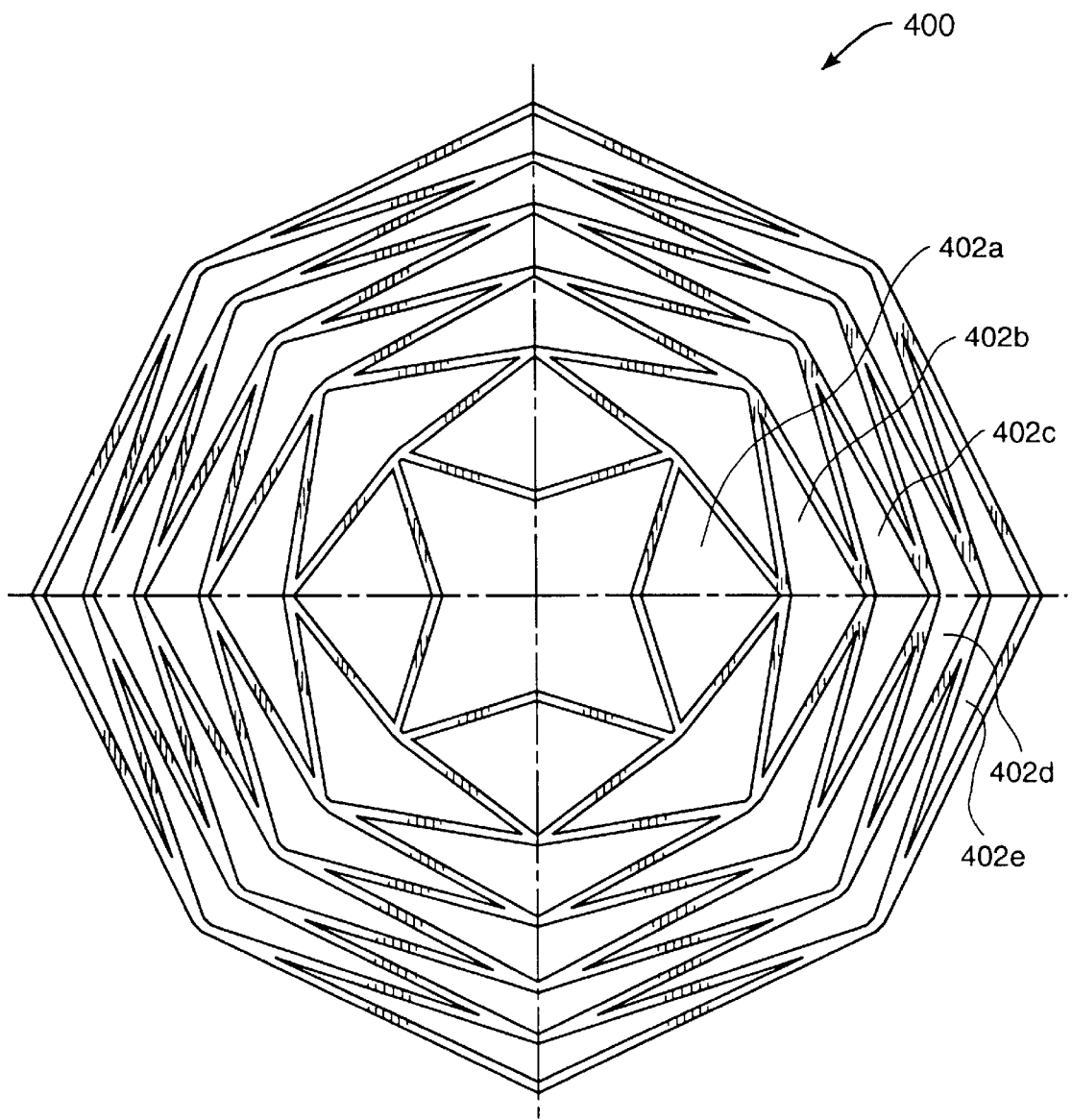
FIG. 16A illustrates a flat stent pattern having a geometry similar to that shown in FIG. 16, except that it includes five successive diamond-shaped elements in tandem and the elements at one end of the resulting cylindrical structure will have an inherently smaller diameter than those at the other end of the cylindrical structure.

Referring to FIG. 16A, an eversible article 400 having a pattern including five rows 402a–402e of lozenge (diamond)-shaped elements is illustrated. Each of the lozenges comprises four beams or struts, and it can be seen that the lengths of the struts of each diamond increase as the row moves radially outward. That is, the struts of diamond 402a are the smallest, the struts of diamond 402b are the next largest, while the struts of diamonds 402c are the next largest, etc., until the struts of diamond 402e are the largest of all. When everted, the planar article 400 will thus form a cylindrical wall having a different structure at one end than at the other end. Usually, the cylindrical wall will have a smaller diameter at the end having diamonds 402a and a larger diameter at the end having diamonds 402e. Such a tapered cylindrical structure will be advantageous whenever it is desired to have a tapered stent or to have a transition region within a larger stent assembly or vascular prosthesis structure. Alternatively, the cylinder resulting from everting the planar article 400 could have a uniform diameter, in which case the diamonds 402a would have to be opened more widely and the diamonds 402e would have to be opened less widely (i.e. be longitudinally extended) in order to maintain an equal diameter.

The tandem stent shown in FIG. 17 can be readily formed from the tandem pattern shown in FIG. 16. This can be accomplished by punching out two of the joined-together patterns by severing the tabs 98. Thereafter, a tapered cylindrical mandrel is provided rather than a cylinder which has been provided with a conical tip. The mandrel is used to transfer the pattern from sheet form into cylindrical form in the manner hereinbefore described by forming the patterns 82 into a cylindrical form in sequence to provide two stents 101 and 102 which are axially aligned and which remain interconnected by the interconnecting portion 97. Thus, in a medical procedure the tandem stents can be used to maintain patency of a vessel over a longer length.

From the foregoing it can be seen that the method of the present invention makes it possible to readily transform planar sheet material into cylindrical material to provide expansible stents. The method of the present invention lends itself to mass production of stents so that they can be made rapidly and inexpensively, even from difficult materials such as nickel titanium alloys.

Figure 18:
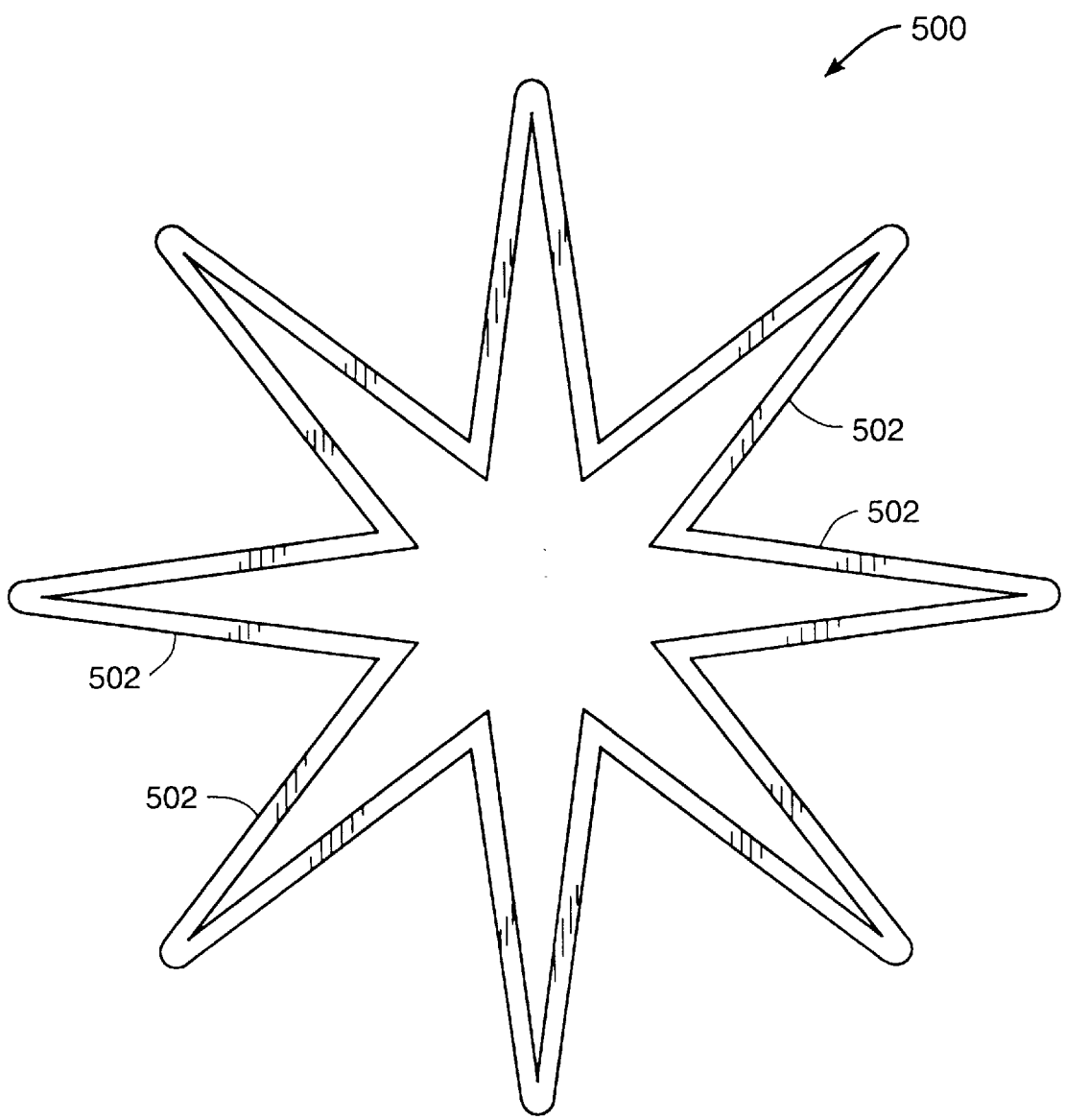
FIG. 18 illustrates a planar eversible structure constructed in accordance with the principles of the present invention, having a continuous annular zig-zag pattern.
Figure 19:
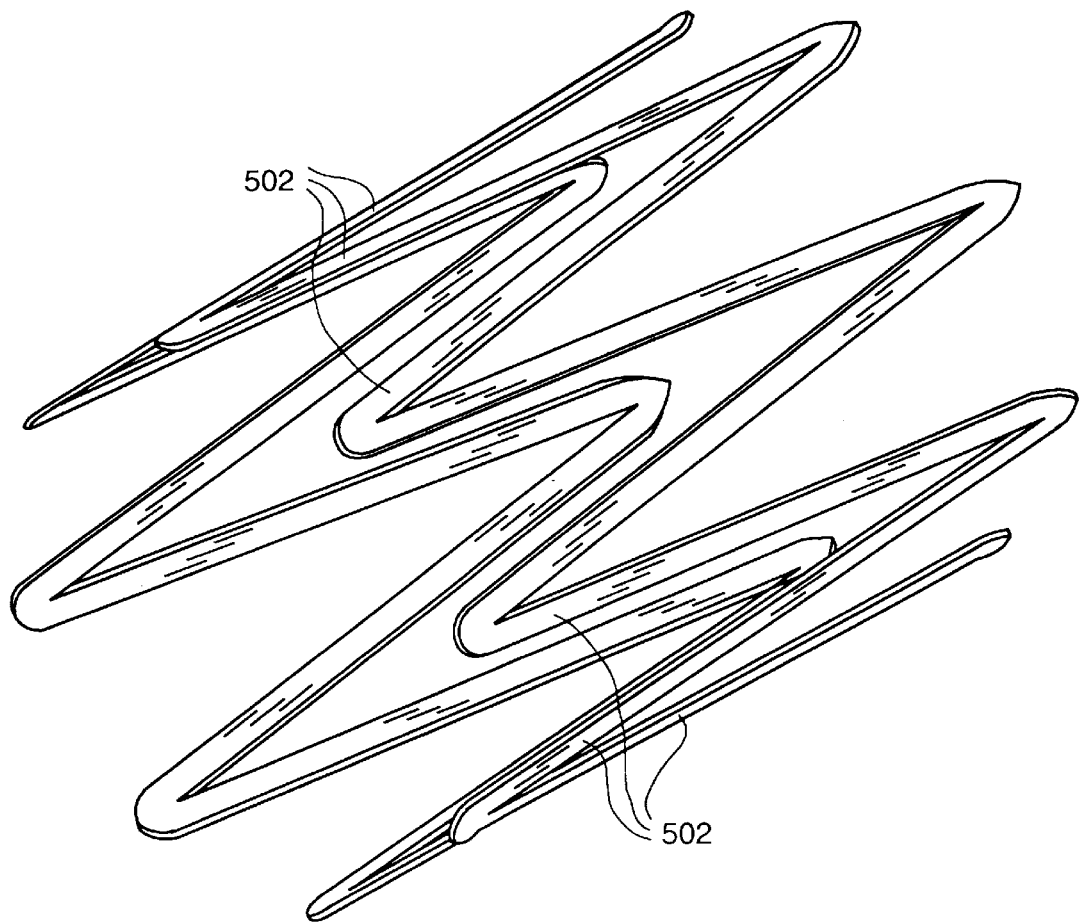
FIG. 19 illustrates the structure of FIG. 18 after it has been everted according to the method of the present invention.

The methods and articles of the present invention may be used to fabricate both complex stent structures as well as relatively simple stent structures. In the latter category, the methods and articles may be used to fabricate a simple zig-zag stent segment which may be utilized by itself or as an assembly of a plurality of longitudinally attached stent segments. A planar eversible article 500 (FIG. 18) is fabricated to have a plurality of generally straight struts 502 in an open star-shaped configuration. The struts 502 are joined as a plurality of circumferentially spaced-apart V-shaped components, with each V-shaped component joined at its radially outward end to the adjacent V-shaped component. The pattern shown in FIG. 18 may be formed by any of the techniques described above, including photochemical etching, cutting, and stamping of a flat sheet of material. Alternatively, each of the struts 502 may be initially be provided as a discrete element, and the individual struts then attached, for example by welding, into the illustrated pattern. The eversible planar article 500 may then be everted into a cylindrical zig-zag stent cylindrical stent segment, as illustrated in FIG. 19.

Figure 20:
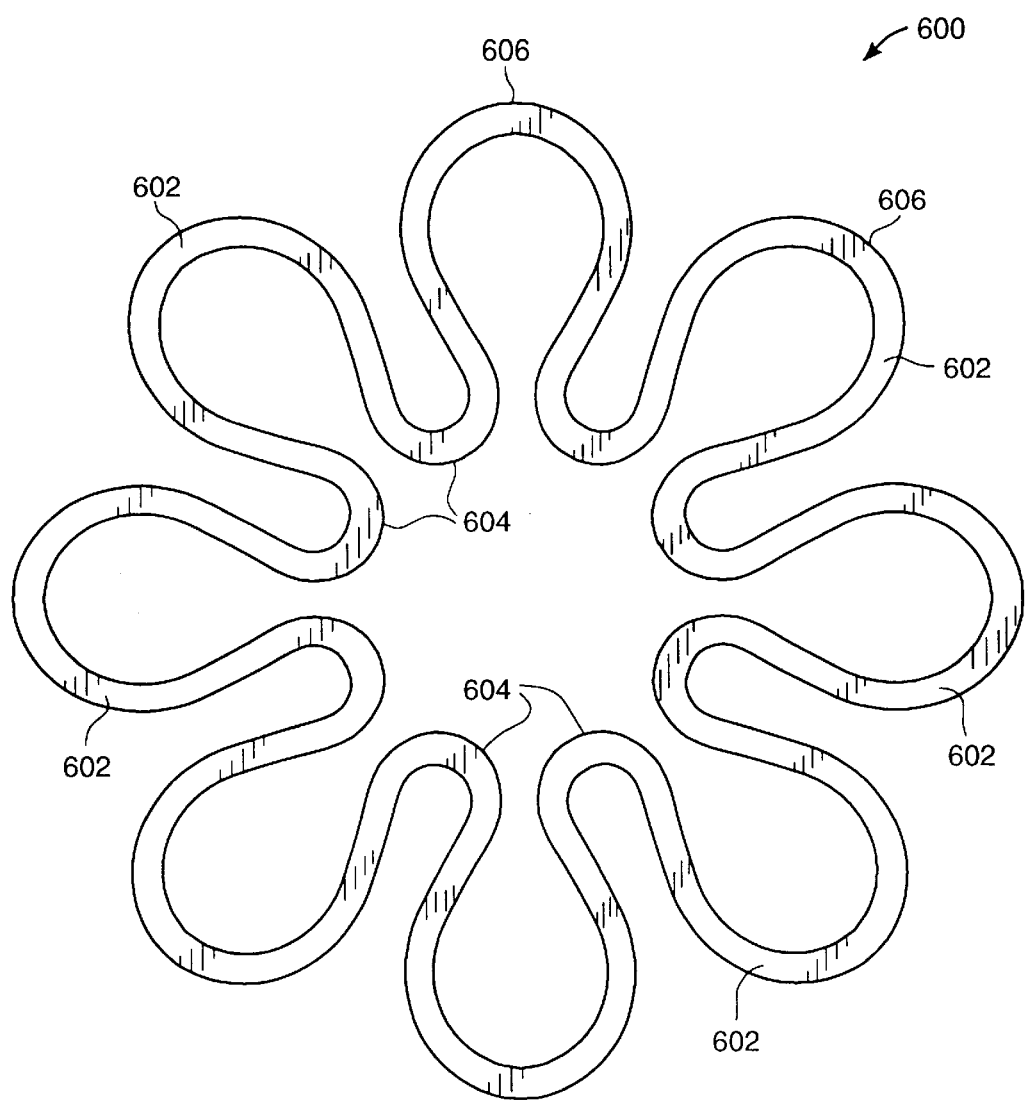
FIG. 20 illustrates a planar eversible structure constructed in accordance with the principles of the present invention, having a continuous annular serpentine pattern.
Figure 21:
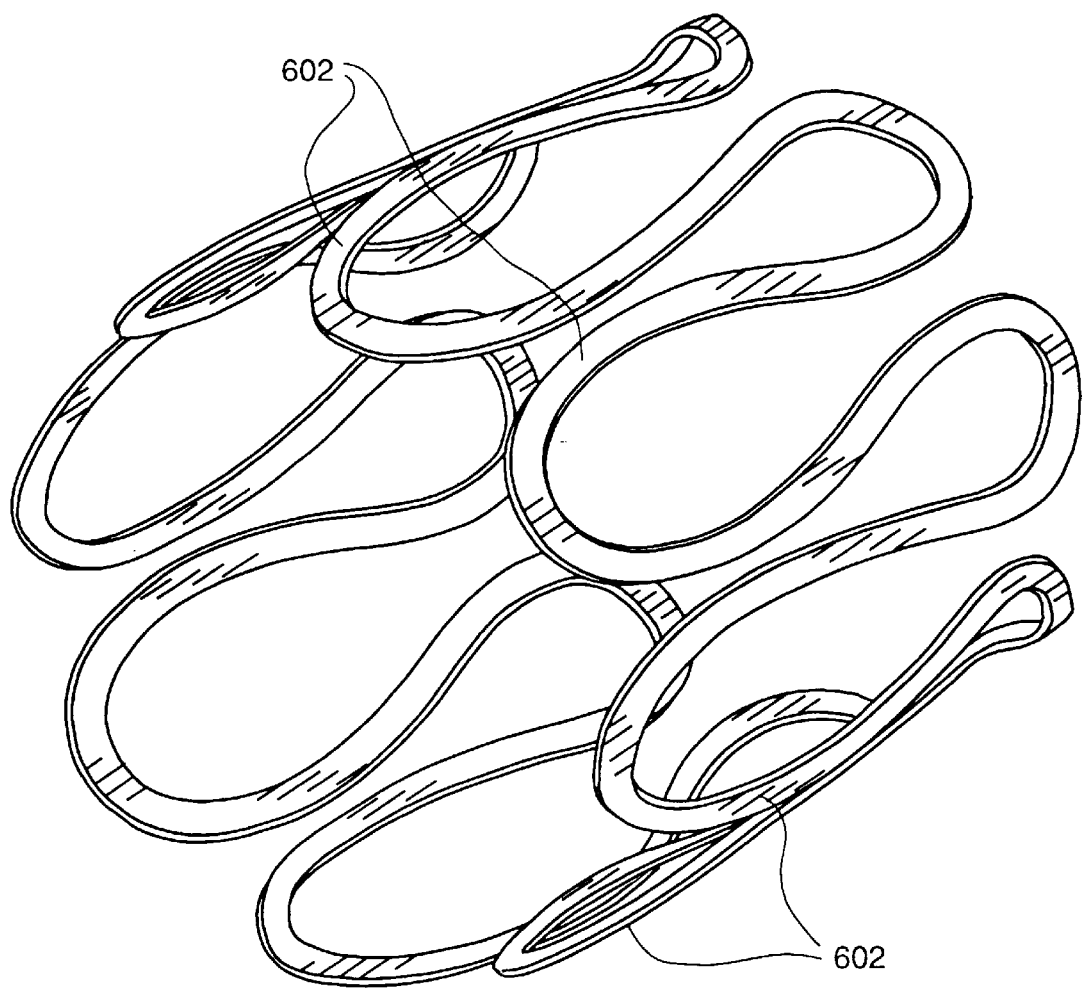
FIG. 21 illustrates the structure of FIG. 20 after it has been everted according to the method of the present invention.

A planar eversible article 600 comprising eight U-shaped elements joined in an annular serpentine pattern as illustrated in FIG. 20. Each of the U-shaped segment 602 has a peripherally inward end 604 and a peripherally outward end 606. By everting the peripherally inward and radially outward and/or the peripherally outward ends 606 radially inward, a cylindrical wall segment comprising a serpentine element is formed, as shown in FIG. 21. The cylindrical element shown in FIG. 21 may be used by itself, or may be joined to form a multiply segmented stent or graft structure in a conventional manner.

Figure 22:
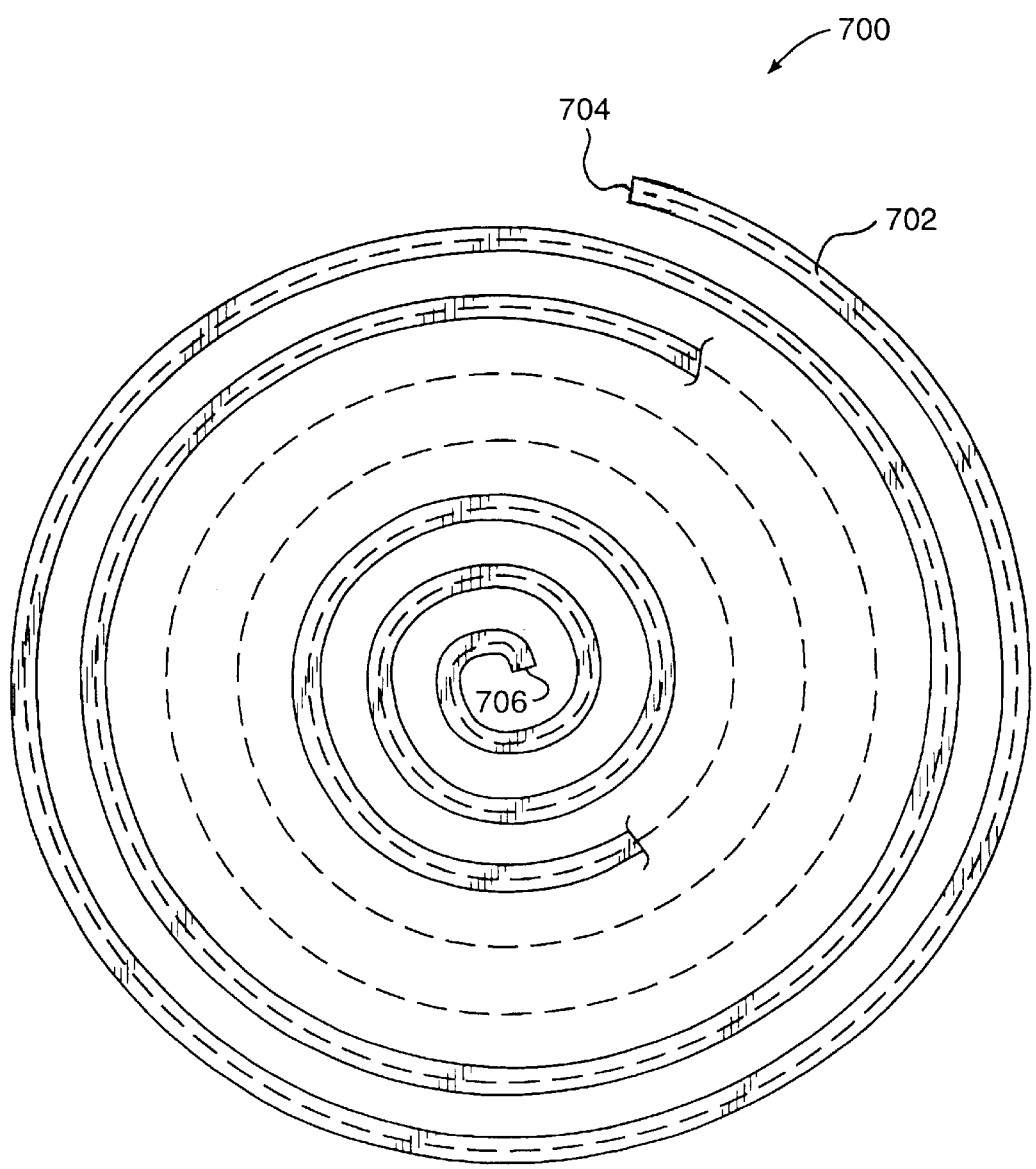
FIG. 22 illustrates a planar eversible structure constructed in accordance with the principles of the present invention, having a discontinuous annular spiral filament.
Figure 23:
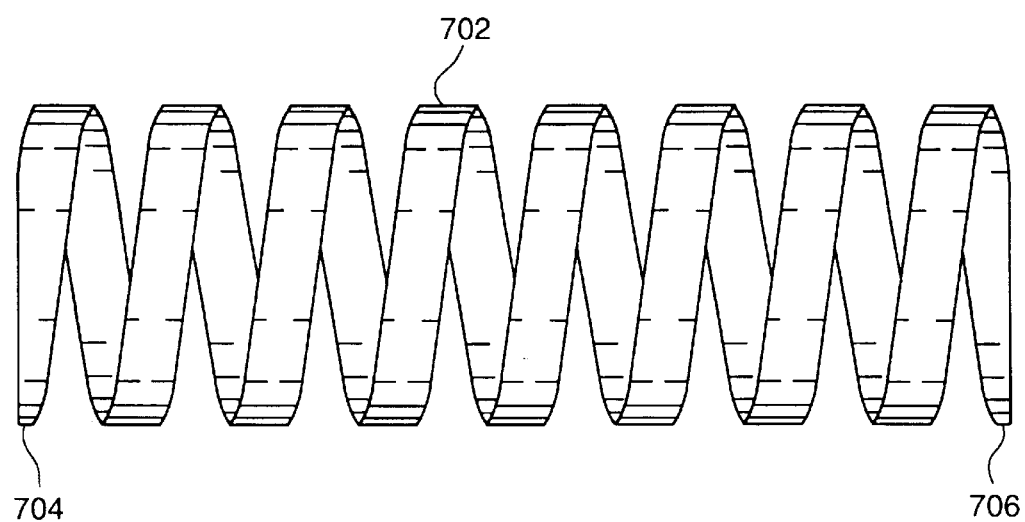
FIG. 23 illustrates the structure of FIG. 22 after it has been everted according to the method of the present invention.

Still another eversible planar structure 700 is illustrated in FIG. 22. The structure 700 comprises a single filament 72, shown in the form of a ribbon, which is spirally wound so that first end 704 lies at a radially outward point and a second end 706 lies at the radially inward point. The spiral, which includes only the single element 702, thus defines the annular lattice which may be everted to form a cylindrical wall segment as shown in FIG. 23.

Figure 24:
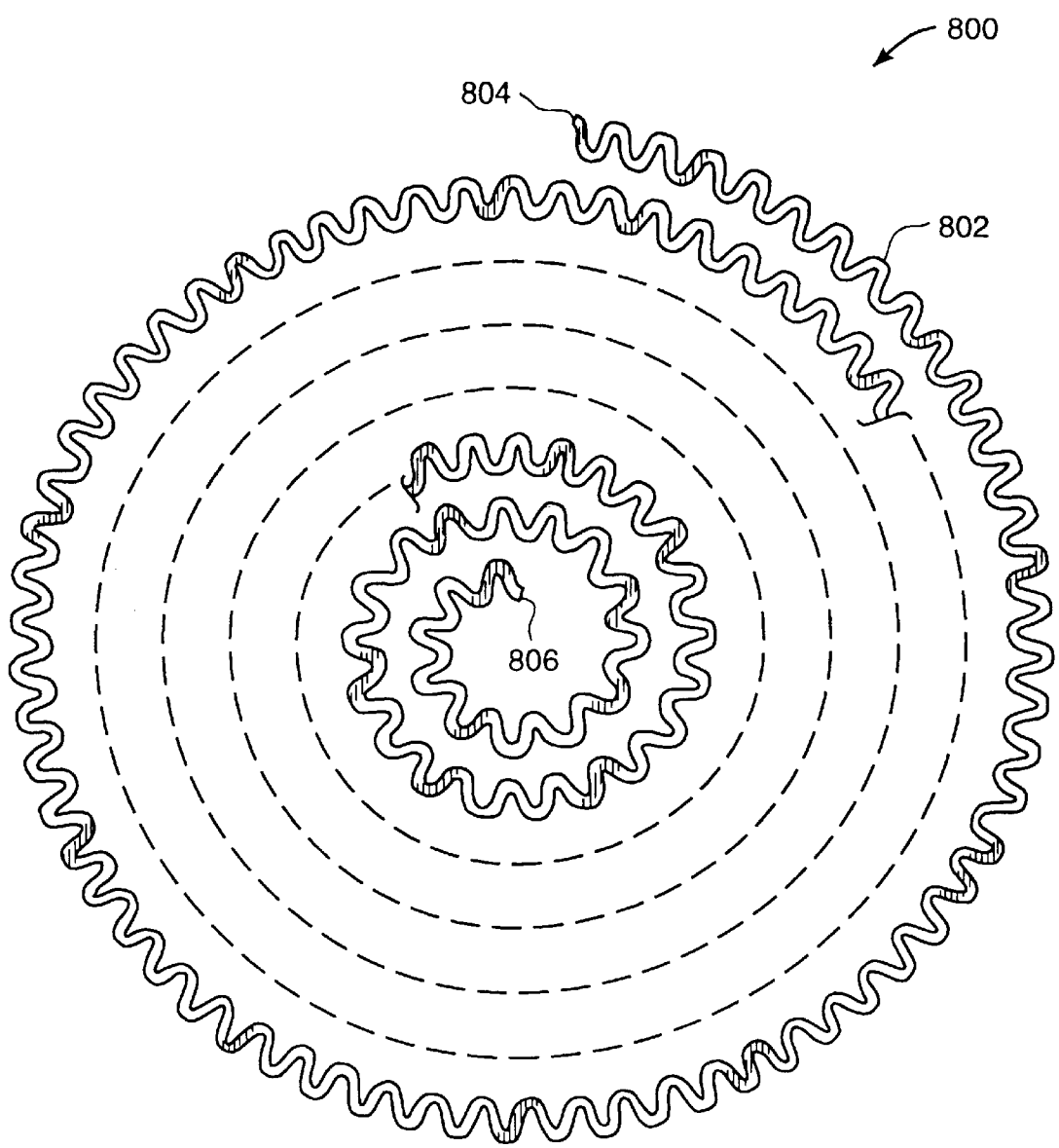
FIG. 24 illustrates a planar eversible structure constructed in accordance with the principles of the present invention, having a discontinuous serpentine spiral element arranged in an annular pattern.
Figure 25:
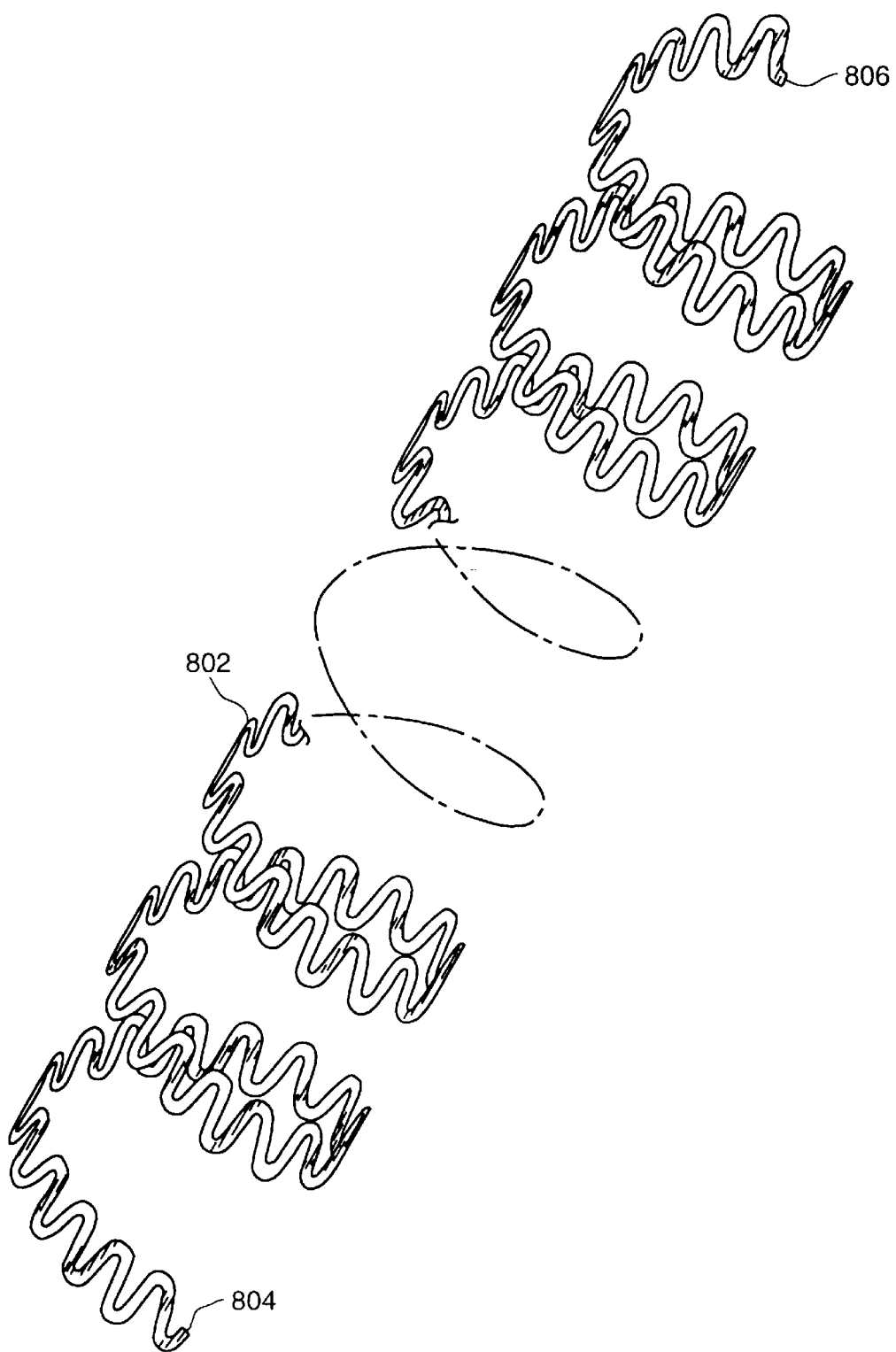
FIG. 25 illustrates the article of FIG. 24 after it has been everted according to the method of the present invention.

A variation of the spiral pattern of FIG. 22 is shown in FIG. 24. Eversible planar article 800 comprises a single spiral element 802 having an outer end 804 and an inner end 806. The spiral element 802, however, is not a single continuously curved element, as shown in FIG. 22, but rather possesses a secondary serpentine pattern superimposed on the spiral. Planar article 800 may be everted to assume the complex helically wound serpentine pattern shown in FIG. 25.

Figure 26:
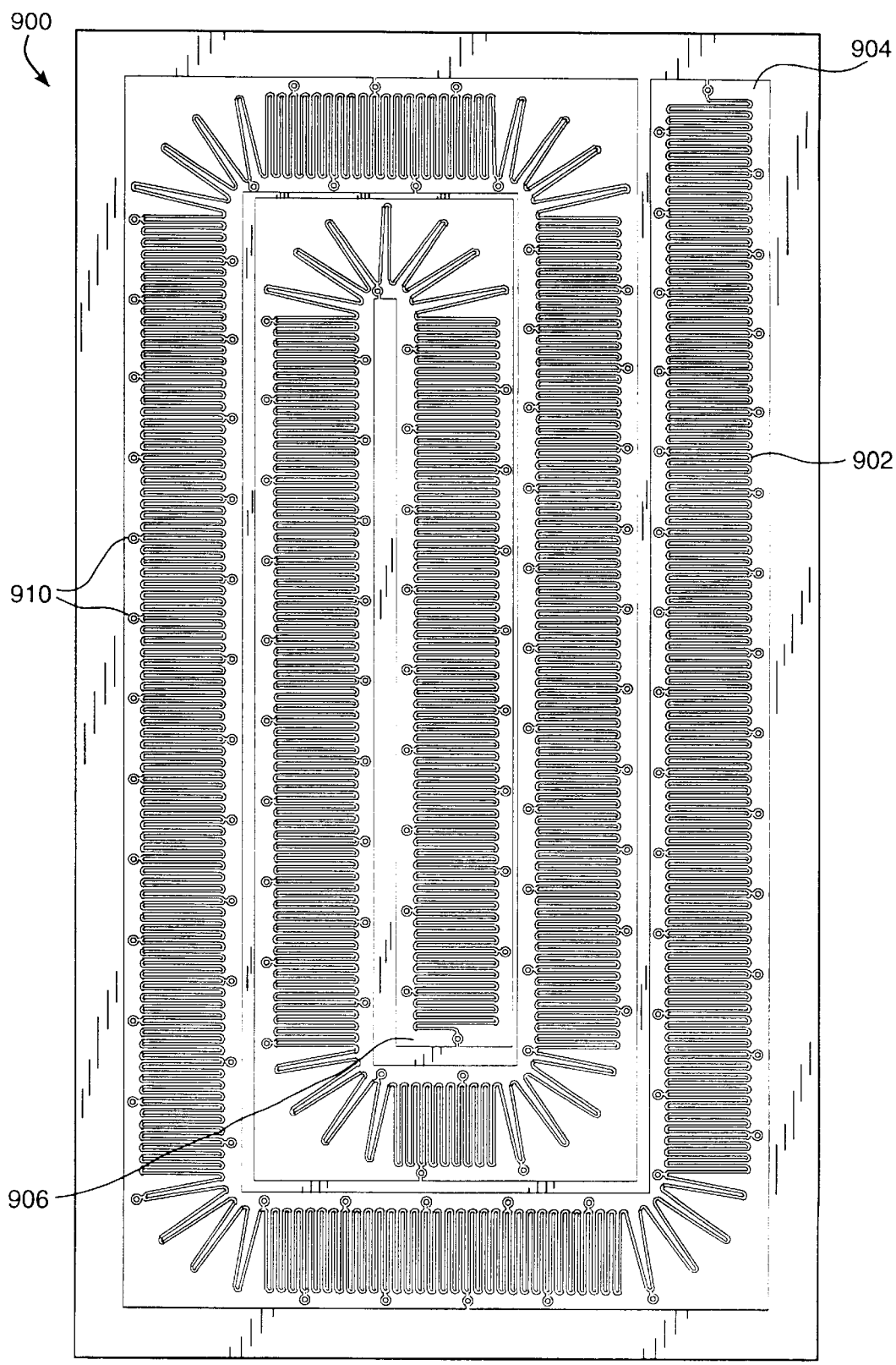
FIG. 26 illustrates a particular spiral eversible article comprising a rectilinear pattern of serpentine elements.
Figure 27:
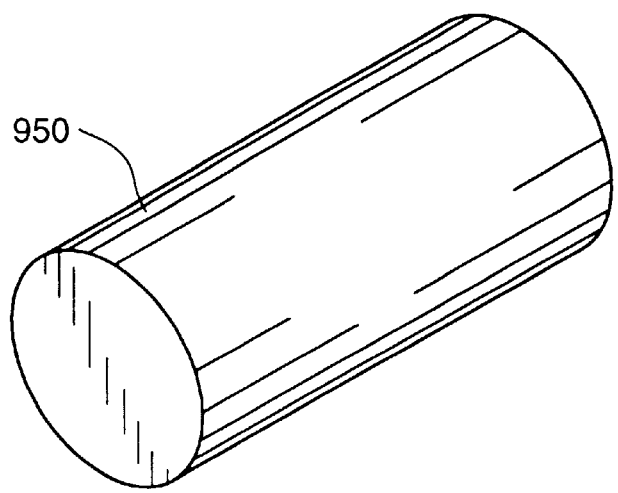
FIG. 27 illustrates cylindrical rod stock that may be used as a starting material for the fabrication methods of the present invention.

Referring now to FIG. 26, a variation on the spiral-serpentine pattern of eversible planar 800 is illustrated. The eversible planar structure 900 of FIG. 26 shows another serpentine element 902 which has been patterned from a flat sheet of material, typically a metal sheet formed by photochemical etching. Instead of being shown in a uniformly curved spiral, however, the eversible planar article 900 is shown in a rectilinear "spiral" pattern, having an outer end 904 and an inner end 906. After removing the serpentine element 902 from its frame, the serpentine element may be everted to form a cylindrical wall portion similar to that shown in FIG. 25. The article 900, however, further includes a plurality of eyelets 910 which permit attachment of sutures, clips, or other fasteners for securing successive turns of the helix together.

Referring now to FIGS. 27–30, methods for forming the eversible planar articles of the present invention from a solid rod 950 of material will be described. The rod 950 may be composed of any of the materials described above and will generally have a circular cross-section. The diameter of the rod will be selected to correspond generally to the diameter of the planar articles which are to be produced. Use of the rod 950 as starting material is thus particularly preferred for forming non-linked cylindrical wall segments. Thus, it will be less useful for forming linked or hinged segments as shown in FIGS. 16 and 17.

Figure 28:
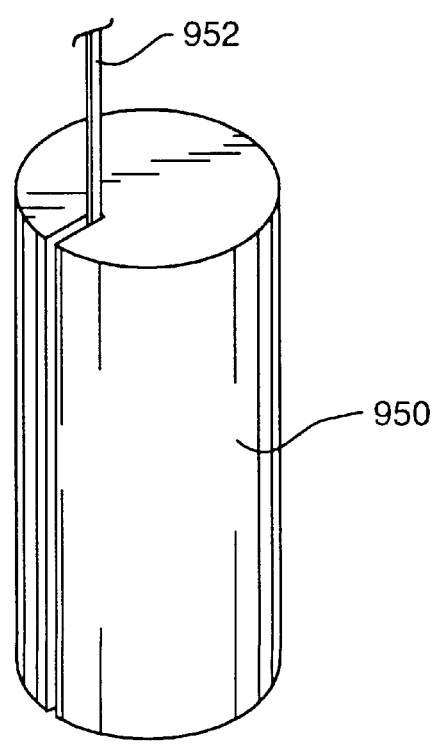
FIG. 28 illustrates a first alternative shaping operation that may be performed on the rod stock of FIG. 27.
Figure 29:
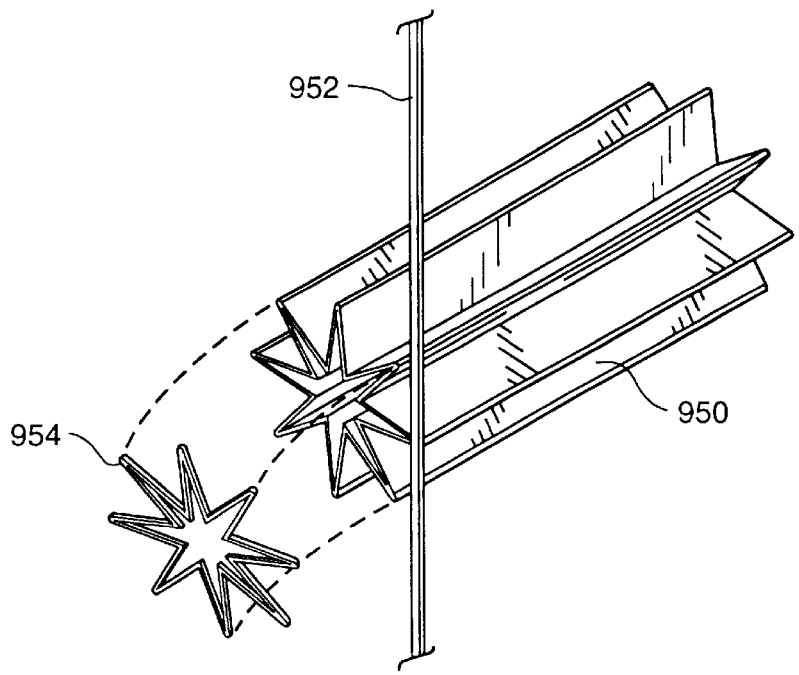
FIG. 29 illustrates the slicing of the rod stock of FIG. 27 after it has been shaped.
Figure 30:
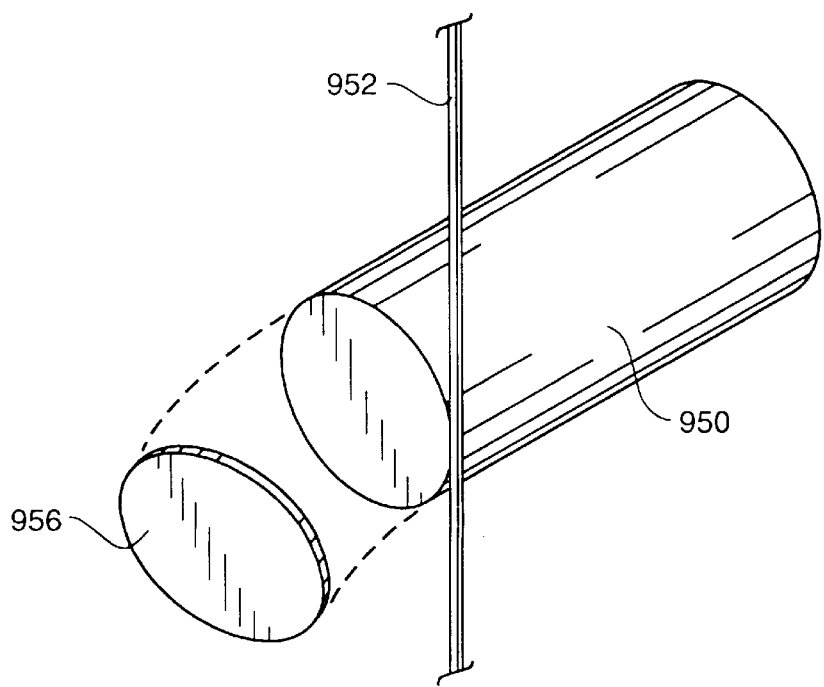
FIG. 30 illustrates an alternative shaping method wherein the rod stock of FIG. 27 is sliced prior to patterning into the eversible articles of the present invention.

The rod stock 950 will have a length suitable for producing a number of discrete eversible planar articles. In particular, the rod stock 950 will eventually be sliced into individual pieces having a desired thickness. Each of the pieces either will have been or will be patterned to have the desired stent geometry, typically by a cutting process, such as EDM. For example, as shown in FIG. 28, the rod stock may first be patterned using an EDM wire 952 in a conventional manner. The exterior of the rod stock 950 may first be patterned, e.g. to obtain a star configuration. Alternatively, the rod stock can be extruded, cast, or micromachined, or otherwise initially formed to have the desired external geometry. In either case, the EDM wire 952 will later be used to form the internal patterns required for the stent geometry. Formation of the internal patterns will usually require that a hole first be drilled or otherwise formed in an axial direction through the rod stock 950 in order to permit access for the EDM wire 952. As shown in FIG. 29, the rod stock 950 may be completely patterned prior to using the EDM wire 952 to slice individual eversible planar articles 954 therefrom. Alternatively, the rod stock 950 may be sliced to produce solid circular blanks 956, as shown in FIG. 30. The blanks 956 may then be stacked and patterned, usually by EDM cutting, to simultaneously form the plurality of individual reversible planar articles. It will usually be desirable to cut or otherwise form the stent geometry before the rod stock 950 is sliced into individual articles since it is difficult to maintain proper alignment of pre-sliced segments 956 during subsequent cutting processes. The present invention, however, contemplates that either the slicing or the patterning steps may be performed first, and in some cases may be performed alternately in order to produce the articles of the present invention.

It is possible to form the articles of the present invention from tube stock in a manner analogous to the use of rod stock just described. The tube stock will have a wall thickness sufficient to accommodate the diameter of the desired planar article. The tube can then be sliced to provide the articles, either before or after patterning. Multiple articles can be obtained from each slice. The advantages of grain uniformity will generally be the same as with rod stock, and fabrication may be somewhat simplified.

Figure 31:
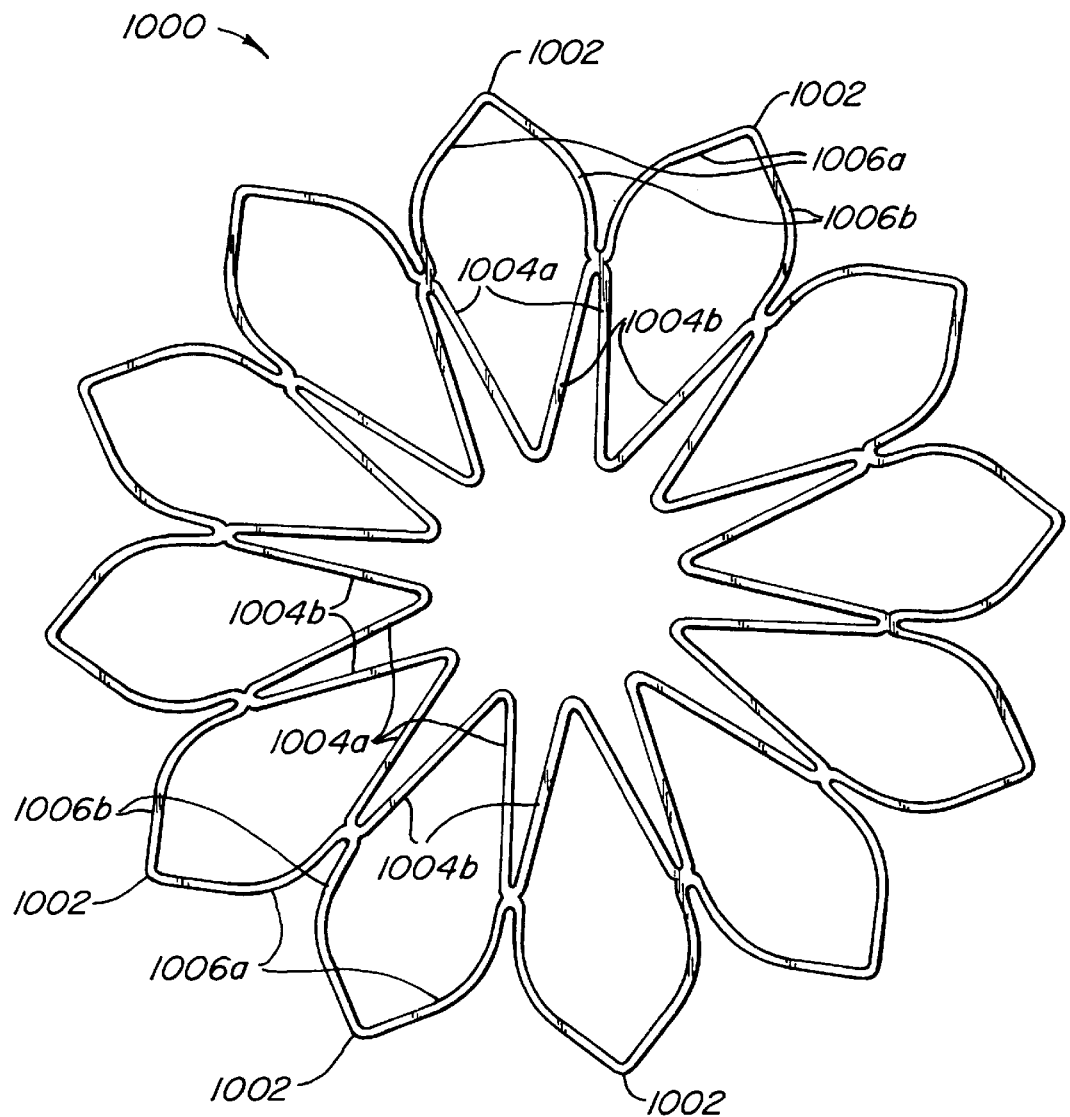
FIG. 31 illustrates another embodiment of the planar eversible article of the present invention, wherein spacing between adjacent lattice elements is increased to facilitate fabrication by photochemical etching.
Figure 32:
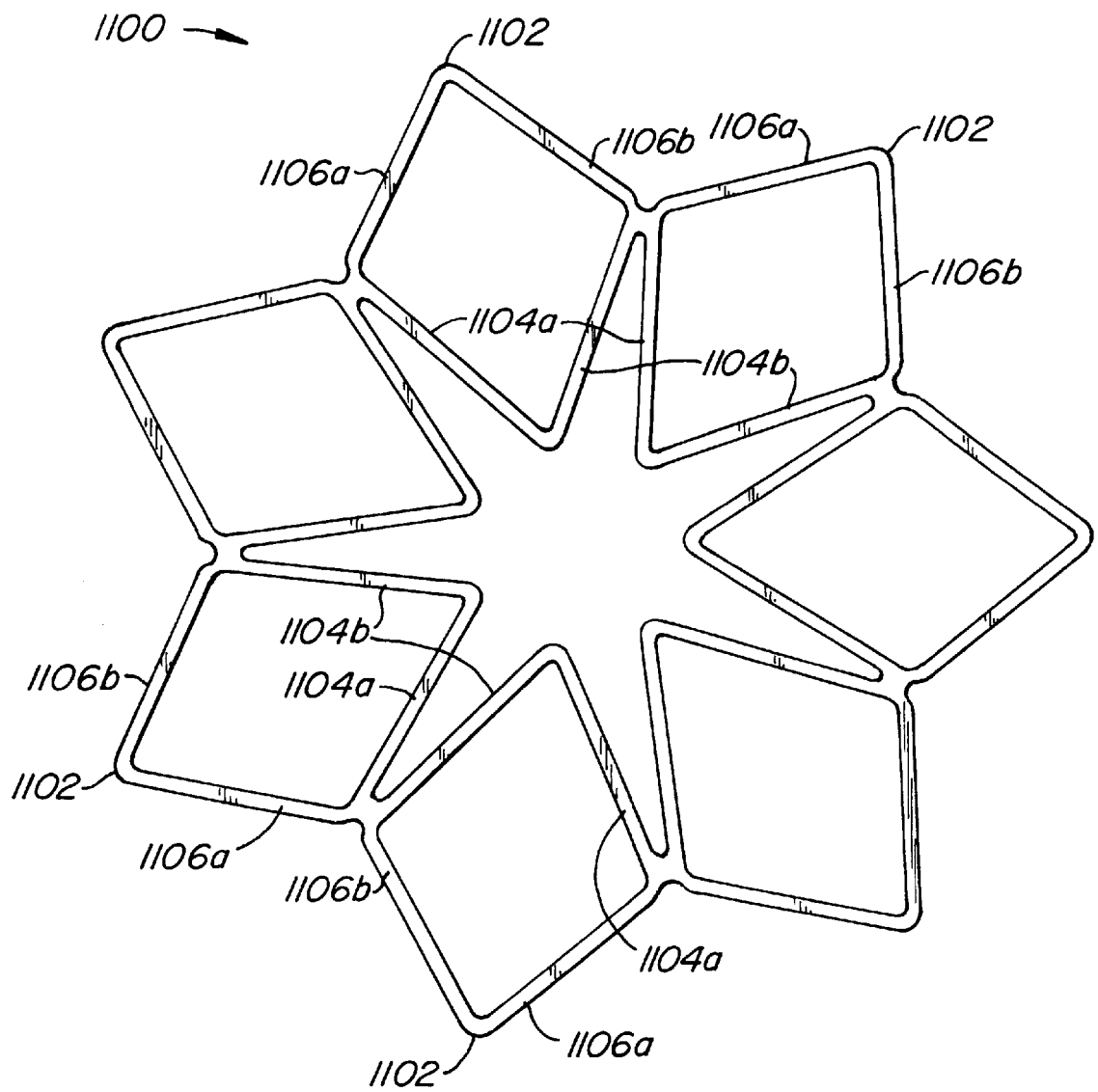
FIG. 32 illustrates yet another embodiment of the planar eversible article of the present invention also having increased spacing between adjacent lattice elements.

Referring now to FIGS. 31 and 32, to planar article patterns which are readily formed by photochemical etching are illustrated. The quality of etching deteriorates when spacing between the etched surfaces becomes too small. In designs, such as the lozenge pattern of FIGS. 2 and 3, the adjacent legs of each lozenge are relatively close, thus decreasing the accuracy and precision of etching. Etching can be improved by patterning the radially inward legs so that they diverge, as shown in FIGS. 31 and 32. In particular, planar article 1000 in FIG. 31 includes eleven tear-drop shaped closed peripheral structures 1002, each of which includes a pair of straight radially inward legs 1004$a$ and 1004$b$. Legs 1004$a$ and 1004$b$ on adjacent structures 1002 diverge to provide sufficient spacing to increase the accuracy and precision of the etch. Radially outward legs 1006$a$ and 1006$b$ are curved. Planar article 1100 in FIG. 32 is similar, with radially inward legs 1004$a$ and 1104$b$ of adjacent structures 1102 diverging. Radially outward legs 1106$a$ and 1106$b$, however, are not curved.

Although the foregoing invention has been described in some detail by way of illustration and example, for purposes of clarity of understanding, it will be obvious that certain changes and modifications may be practiced within the scope of the appended claims.

What is claimed is:

1. A method for fabricating a planar eversible lattice which when everted forms a cylindrical wall of a cylindrical stent, said method comprising:

patterning a planar sheet of material to form an annular lattice of interconnected elements defining the eversible structure, wherein the eversible structure becomes radially expansible after eversion.

2. A method as in claim 1, wherein the interconnected elements of the planar annular lattice are joined in at least one continuous annular path.

3. A method as in claim 2, wherein the interconnected elements comprise an annular serpentine ring.

4. A method as in claim 1, wherein the eversible lattice is an annular serpentine ring which becomes a cylindrical serpentine ring after eversion.

5. A method as in claim 1, wherein the interconnected elements comprise a plurality of closed peripheral structures.

6. A method as in claim 1, wherein the closed peripheral structures are polygonal.

7. A method as in claim 6, wherein the polygonal structures are lozenge-shaped.

8. A method as in claim 7, wherein the eversible lattice comprises a plurality of lozenge-shaped elements having axes which are aligned radially within the annular lattice, wherein adjacent lozenge-shaped elements are connected to each other.

9. A method as in claim 8, wherein the adjacent lozenge-shaped elements are connected to each other by tabs located along a common diametric line within the annular lattice.

10. A method as in claim 9, wherein the eversible lattice comprises at least two radially successive annular rows of lozenge-shaped elements.

11. A method as in claim 1, wherein the patterning step comprises photochemical etching of the planar sheet of material.

12. A method as in claim 1, wherein the patterning step comprises cutting the sheet of material.

13. A method as in claim 12, wherein the cutting step comprises electrical discharge machining.

14. A method as in claim 12, wherein the cutting step comprises laser cutting.

15. A method as in claim 12, wherein the cutting step comprises providing a plurality of planar sheets arranged in a stack and cutting the stack to provide a plurality of planar networks.

16. A method as in claim 1, wherein the patterning step comprises stamping the planar sheet of material.

17. A method as in claim 1, wherein the planar annular lattice of interconnected elements is composed of a metal.

18. A method as in claim 17, wherein the metal is a shape memory alloy.

19. A method as in claim 18, wherein the metal is a nickel titanium alloy.

20. A method as in claim 19, wherein the metal is selected from the group consisting of stainless steel, titanium, tantalum, platinum, and elgiloy.

* * * * *

UNITED STATES PATENT AND TRADEMARK OFFICE
CERTIFICATE OF CORRECTION

PATENT NO. : 6,327,772 B1
DATED : December 11, 2001
INVENTOR(S) : Zadno-Azizi et al.

It is certified that error appears in the above-identified patent and that said Letters Patent is hereby corrected as shown below:

<u>Column 15,</u>
Line 4, please delete "1" and insert -- 5 --.

Signed and Sealed this

Fifth Day of November, 2002

*Attest:*

*Attesting Officer*

JAMES E. ROGAN
*Director of the United States Patent and Trademark Office*